(12) United States Patent
Girdhar et al.

(10) Patent No.: US 11,944,374 B2
(45) Date of Patent: Apr. 2, 2024

(54) ELECTRICAL SIGNALS FOR RETRIEVAL OF MATERIAL FROM VESSEL LUMENS

(71) Applicant: Covidien LP, Mansfield, MA (US)

(72) Inventors: Gaurav Girdhar, Anaheim Hills, CA (US); Hoai Nguyen, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 249 days.

(21) Appl. No.: 17/446,407

(22) Filed: Aug. 30, 2021

(65) Prior Publication Data

US 2023/0064470 A1 Mar. 2, 2023

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 17/221* (2013.01);
(Continued)

(58) Field of Classification Search
CPC .. A61B 2018/0072; A61B 2018/00726; A61B 2018/0041
See application file for complete search history.

(56) References Cited

U.S. PATENT DOCUMENTS

| 5,549,626 A | 8/1996 | Miller et al. |
| 5,928,260 A | 7/1999 | Chin et al. |

(Continued)

FOREIGN PATENT DOCUMENTS

| CN | 101472685 A | 7/2009 |
| CN | 104884681 B | 5/2018 |

(Continued)

OTHER PUBLICATIONS

Chon CH, Qin Z, Kwok JC, Lam DC. Mechanical behavior of rf-treated thrombus in mechanical thrombectomy. Med Eng Phys. Sep. 2017;47:184-189. doi: 10.1016/j.medengphy.2017.06.011. Epub Jul. 5, 2017. PMID: 28688756. (Year: 2017).*

(Continued)

*Primary Examiner* — Jaymi E Della
(74) *Attorney, Agent, or Firm* — Fortem IP LLP; Connie Cheng

(57) ABSTRACT

Devices, systems, and methods for removing obstructions from body lumens are disclosed herein. In some embodiments, a system for removing a thrombus includes an interventional element configured to be disposed proximate to or adjacent to a thrombus within a blood vessel. The system can include a signal generator in electrical communication with the interventional element. The signal generator can be configured to deliver an electrical signal to the interventional element. The electrical signal can include a waveform having a positive phase having a peak positive current and a first duration, and a negative phase having a peak negative current and a second duration. A magnitude of the peak positive current can be greater than a magnitude of the peak negative current, and the first duration can be greater than the second duration.

22 Claims, 13 Drawing Sheets

(51) Int. Cl.
*A61B 17/221* (2006.01)
*A61B 18/00* (2006.01)

(52) U.S. Cl.
CPC .............. *A61B 2018/00077* (2013.01); *A61B 2018/00214* (2013.01); *A61B 2018/0041* (2013.01); *A61B 2018/0072* (2013.01); *A61B 2018/00726* (2013.01); *A61B 2018/1422* (2013.01); *A61B 2018/1435* (2013.01)

(56) References Cited

U.S. PATENT DOCUMENTS

| | | |
|---|---|---|
| 5,972,019 A | 10/1999 | Engelson et al. |
| 6,022,336 A | 2/2000 | Zadno-Azizi et al. |
| 6,059,779 A | 5/2000 | Mills |
| 6,315,794 B1 | 11/2001 | Richter |
| 6,540,733 B2 | 4/2003 | Constantz et al. |
| 6,663,650 B2 | 12/2003 | Sepetka et al. |
| 7,094,249 B1 | 8/2006 | Broome et al. |
| 7,520,966 B2 | 4/2009 | Diaz et al. |
| 7,556,624 B2 | 7/2009 | Laufer et al. |
| 8,038,674 B2 | 10/2011 | Schmaltz et al. |
| 8,382,821 B2 | 2/2013 | Richter |
| 8,603,014 B2 | 12/2013 | Alleman et al. |
| 8,837,800 B1 | 9/2014 | Bammer et al. |
| 8,888,788 B2 | 11/2014 | Adams et al. |
| 8,965,534 B2 | 2/2015 | Hyatt et al. |
| 9,011,431 B2 | 4/2015 | Long et al. |
| 9,039,753 B2 | 5/2015 | Thramann |
| 9,119,656 B2 | 9/2015 | Bose et al. |
| 9,126,018 B1 | 9/2015 | Garrison |
| 9,179,971 B2 | 11/2015 | Kirschenman |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,681,882 B2 | 6/2017 | Wilson et al. |
| 9,713,730 B2 | 7/2017 | Mathur et al. |
| 9,737,318 B2 | 8/2017 | Monstadt et al. |
| 9,770,251 B2 | 9/2017 | Bowman et al. |
| 9,795,400 B2 | 10/2017 | Davidson |
| 9,801,643 B2 | 10/2017 | Hansen et al. |
| 9,808,271 B2 | 11/2017 | Ulm |
| 9,827,084 B2 | 11/2017 | Bonnette et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,092,241 B2 | 10/2018 | Toth et al. |
| 10,251,569 B2 | 4/2019 | Burkett |
| 10,709,463 B2 | 7/2020 | Girdhar et al. |
| 10,987,117 B2 | 4/2021 | Girdhar et al. |
| 11,058,444 B2 | 7/2021 | Girdhar et al. |
| 11,090,071 B2 | 8/2021 | Girdhar et al. |
| 2001/0001314 A1 | 5/2001 | Davison et al. |
| 2002/0059938 A1 | 5/2002 | Fogarty et al. |
| 2002/0133111 A1 | 9/2002 | Shadduck et al. |
| 2004/0073243 A1* | 4/2004 | Sepetka .................. A61F 2/013 606/159 |
| 2004/0219660 A1 | 11/2004 | Dev et al. |
| 2005/0228417 A1 | 10/2005 | Teitelbaum et al. |
| 2006/0089638 A1 | 4/2006 | Carmel et al. |
| 2008/0042662 A1 | 2/2008 | Abraham |
| 2008/0045881 A1 | 2/2008 | Teitelbaum et al. |
| 2008/0262489 A1 | 10/2008 | Steinke et al. |
| 2008/0294181 A1 | 11/2008 | Wensel et al. |
| 2009/0054918 A1 | 2/2009 | Henson |
| 2009/0069828 A1 | 3/2009 | Martin et al. |
| 2009/0318892 A1 | 12/2009 | Aboytes et al. |
| 2010/0004623 A1 | 1/2010 | Hamilton et al. |
| 2010/0010533 A1 | 1/2010 | Burke et al. |
| 2010/0042136 A1 | 2/2010 | Berrada et al. |
| 2010/0228280 A1 | 9/2010 | Groothuis et al. |
| 2010/0256627 A1 | 10/2010 | Ma et al. |
| 2011/0130756 A1 | 6/2011 | Everson et al. |
| 2011/0196478 A1 | 8/2011 | Torosoff |
| 2011/0202085 A1 | 8/2011 | Loganathan et al. |
| 2011/0301549 A1 | 12/2011 | Hartmann |
| 2011/0301594 A1* | 12/2011 | Orion .................. A61B 18/1492 606/41 |
| 2013/0008780 A1 | 1/2013 | Andreacchi et al. |
| 2013/0030461 A1 | 1/2013 | Marks et al. |
| 2013/0072960 A1 | 3/2013 | Schneider et al. |
| 2013/0281788 A1 | 10/2013 | Garrison |
| 2013/0282084 A1 | 10/2013 | Mathur et al. |
| 2013/0345739 A1 | 12/2013 | Brady et al. |
| 2014/0025152 A1 | 1/2014 | Headley |
| 2014/0172001 A1 | 6/2014 | Becking et al. |
| 2014/0188127 A1 | 7/2014 | Dubrul et al. |
| 2014/0276074 A1 | 9/2014 | Warner |
| 2014/0277013 A1 | 9/2014 | Sepetka et al. |
| 2014/0277079 A1 | 9/2014 | Vale et al. |
| 2014/0309673 A1 | 10/2014 | Dacuycuy et al. |
| 2014/0309675 A1 | 10/2014 | Maisano et al. |
| 2014/0343595 A1 | 11/2014 | Monstadt et al. |
| 2014/0364896 A1 | 12/2014 | Consigny |
| 2015/0133990 A1 | 5/2015 | Davidson |
| 2015/0150672 A1 | 6/2015 | Ma |
| 2015/0297251 A1 | 10/2015 | Sos |
| 2015/0359547 A1 | 12/2015 | Vale et al. |
| 2016/0008003 A1 | 1/2016 | Kleshinski et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0228681 A1 | 8/2016 | Di Palma et al. |
| 2016/0242661 A1 | 8/2016 | Fischell et al. |
| 2016/0296690 A1 | 10/2016 | Kume et al. |
| 2016/0302808 A1 | 10/2016 | Loganathan et al. |
| 2016/0331377 A1 | 11/2016 | Divino et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0215955 A1 | 8/2017 | Hancock et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0367707 A1 | 12/2017 | Divino |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0133436 A1 | 5/2018 | Garrison et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0161541 A1 | 6/2018 | Haldis et al. |
| 2018/0185614 A1 | 7/2018 | Garrison et al. |
| 2018/0200040 A1 | 7/2018 | Wasdyke et al. |
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |

(56) References Cited

U.S. PATENT DOCUMENTS

| | | |
|---|---|---|
| 2019/0046119 A1 | 2/2019 | Oxley |
| 2019/0239910 A1 | 8/2019 | Brady et al. |
| 2019/0262069 A1* | 8/2019 | Taff .................. A61B 18/00 |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1 | 12/2019 | Nguyen et al. |
| 2020/0129742 A1 | 4/2020 | Cope et al. |
| 2020/0297367 A1 | 9/2020 | Girdhar et al. |
| 2020/0297410 A1 | 9/2020 | Nguyen et al. |
| 2020/0390455 A1 | 12/2020 | Nguyen et al. |
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0068853 A1 | 3/2021 | Nguyen et al. |
| 2021/0177427 A1 | 6/2021 | Nguyen et al. |
| 2021/0177442 A1 | 6/2021 | Girdhar et al. |
| 2021/0177446 A1 | 6/2021 | Girdhar et al. |
| 2021/0186540 A1 | 6/2021 | Taff et al. |
| 2021/0238764 A1 | 8/2021 | Tyvoll et al. |
| 2022/0202431 A1 | 6/2022 | Davidson et al. |
| 2022/0236569 A1 | 7/2022 | Yamazaki et al. |
| 2022/0387051 A1 | 12/2022 | Girdhar et al. |
| 2022/0387098 A1 | 12/2022 | Girdhar et al. |

FOREIGN PATENT DOCUMENTS

| | | | |
|---|---|---|---|
| EP | 1484025 A1 | 12/2004 | |
| EP | 2319575 B1 | 11/2013 | |
| EP | 2490764 B1 | 9/2014 | |
| EP | 2895645 A1 | 7/2015 | |
| EP | 2967605 A1 | 1/2016 | |
| EP | 3184067 A1 | 6/2017 | |
| JP | 10290805 A | 11/1998 | |
| JP | 2014004219 A | 1/2014 | |
| JP | 2018118132 A | 8/2018 | |
| KR | 20180102877 A | 9/2018 | |
| WO | 2009127037 A1 | 10/2009 | |
| WO | 2010061376 A1 | 6/2010 | |
| WO | 2014079148 A1 | 5/2014 | |
| WO | 2015141317 A1 | 9/2015 | |
| WO | 2016198947 A1 | 12/2016 | |
| WO | 2017192999 A1 | 11/2017 | |
| WO | 2018019829 A1 | 2/2018 | |
| WO | 2018033401 A1 | 2/2018 | |
| WO | 2018046408 A2 | 3/2018 | |
| WO | 2018127796 A1 | 7/2018 | |
| WO | 2018137029 A1 | 8/2018 | |
| WO | 2018137030 A1 | 8/2018 | |
| WO | 2018145212 A1 | 8/2018 | |
| WO | 2018156813 A1 | 8/2018 | |
| WO | 2018172891 A1 | 9/2018 | |
| WO | 2018187776 A1 | 10/2018 | |
| WO | 2019102307 A1 | 5/2019 | |
| WO | WO-2019133608 A1 * | 7/2019 | ......... A61B 18/1492 |
| WO | 2019246377 A2 | 12/2019 | |
| WO | 2020174326 A1 | 9/2020 | |

OTHER PUBLICATIONS

International Search Report and Written Opinion dated Mar. 24, 2022; International Application No. PCT/US2021/061540; 10 pages.

Extended European Search Report dated Jul. 15, 2021; European Application No. 18888795.4; 6 pages.

International Search Report and Written Opinion dated Feb. 26, 2021; International Application No. PCT/US20/63200; 14 pages.

International Search Report and Written Opinion dated May 25, 2020, International Application No. PCT/US20/22463, 10 pages.

International Search Report and Written Opinion dated Nov. 3, 2020, International Application No. PCT/US20/70142, 18 pages.

Fort, Stephen , et al., "'Fused-Gold' vs. 'Bare' stainless steel NIRflex stents of the same geometric design in diseased native coronary arteries. Long-term results from the NIR TOP Study", Euro Interv 2007; 3:256-261.

* cited by examiner

| Example | Peak Positive Current (mA) | Peak Negative Current (mA) | Positive Duty Cycle (%) | Negative Duty Cycle (%) | Frequency (Hz) | Peak Voltage (Volts) | Positive Pulse Width (ms) | Total Time (min) | Total Positive Charge (mC) | Peak Power (mW) | Total Energy Supplied (mJ) |
|---|---|---|---|---|---|---|---|---|---|---|---|
| 1 | 1 | -0.1 | 90 | 10 | 1000 | 1 | 0.9 | 2 | 108 | 1 | 108 |
| 2 | 2 | -0.1 | 90 | 10 | 1000 | 2 | 0.9 | 2 | 216 | 4 | 432 |
| 3 | 2.5 | -0.1 | 90 | 10 | 1000 | 2.5 | 0.9 | 2 | 270 | 6.25 | 675 |
| 4 | 3 | -0.1 | 90 | 10 | 1000 | 3 | 0.9 | 2 | 324 | 9 | 972 |
| 5 | 1 | -0.2 | 90 | 10 | 1000 | 1 | 0.9 | 2 | 108 | 1 | 108 |
| 6 | 2 | -0.2 | 90 | 10 | 1000 | 2 | 0.9 | 2 | 216 | 4 | 432 |
| 7 | 2.5 | -0.2 | 90 | 10 | 1000 | 2.5 | 0.9 | 2 | 270 | 6.25 | 675 |
| 8 | 3 | -0.2 | 90 | 10 | 1000 | 3 | 0.9 | 2 | 324 | 9 | 972 |
| 9 | 1 | -0.1 | 95 | 5 | 1000 | 1 | 0.95 | 2 | 114 | 1 | 114 |
| 10 | 2 | -0.1 | 95 | 5 | 1000 | 2 | 0.95 | 2 | 228 | 4 | 456 |
| 11 | 2.5 | -0.1 | 95 | 5 | 1000 | 2.5 | 0.95 | 2 | 285 | 6.25 | 712.5 |
| 12 | 3 | -0.1 | 95 | 5 | 1000 | 3 | 0.95 | 2 | 342 | 9 | 1026 |
| 13 | 1 | -0.2 | 95 | 5 | 1000 | 1 | 0.95 | 2 | 114 | 1 | 114 |
| 14 | 2 | -0.2 | 95 | 5 | 1000 | 2 | 0.95 | 2 | 228 | 4 | 456 |
| 15 | 2.5 | -0.2 | 95 | 5 | 1000 | 2.5 | 0.95 | 2 | 285 | 6.25 | 712.5 |
| 16 | 3 | -0.2 | 95 | 5 | 1000 | 3 | 0.95 | 2 | 342 | 9 | 1026 |
| 17 | 1 | -0.2 | 75 | 25 | 100 | 1 | 7.5 | 3 | 135 | 1 | 135 |
| 18 | 2 | -0.2 | 75 | 25 | 100 | 2 | 7.5 | 4 | 360 | 4 | 720 |
| 19 | 2.5 | -0.2 | 75 | 25 | 100 | 2.5 | 7.5 | 5 | 562.5 | 6.25 | 1406.25 |
| 20 | 3 | -0.2 | 75 | 25 | 100 | 3 | 7.5 | 6 | 810 | 9 | 2430 |
| 21 | 1 | -0.2 | 75 | 25 | 10000 | 1 | 0.075 | 7 | 315 | 1 | 315 |
| 22 | 2 | -0.2 | 75 | 25 | 10000 | 2 | 0.075 | 8 | 720 | 4 | 1440 |
| 23 | 2.5 | -0.2 | 75 | 25 | 10000 | 2.5 | 0.075 | 9 | 1012.5 | 6.25 | 2531.25 |
| 24 | 3 | -0.2 | 75 | 25 | 10000 | 3 | 0.075 | 10 | 1350 | 9 | 4050 |

FIG. 6A

| Example | Peak Positive Current (mA) | Peak Negative Current (mA) | Positive Duty Cycle (%) | Negative Duty Cycle (%) | Frequency (Hz) | Peak Voltage (Volts) | Positive Pulse Width (ms) | Total Time (min) | Total Positive Charge (mC) | Peak Power (mW) | Total Energy Supplied (mJ) |
|---|---|---|---|---|---|---|---|---|---|---|---|
| 25 | 1 | -0.1 | 90 | 10 | 1000 | 0.05 | 0.9 | 2 | 108 | 0.05 | 5.4 |
| 26 | 2 | -0.1 | 90 | 10 | 1000 | 0.1 | 0.9 | 2 | 216 | 0.2 | 21.6 |
| 27 | 2.5 | -0.1 | 90 | 10 | 1000 | 0.125 | 0.9 | 2 | 270 | 0.3125 | 33.75 |
| 28 | 3 | -0.1 | 90 | 10 | 1000 | 0.15 | 0.9 | 2 | 324 | 0.45 | 48.6 |
| 29 | 1 | -0.2 | 90 | 10 | 1000 | 0.05 | 0.9 | 2 | 108 | 0.05 | 5.4 |
| 30 | 2 | -0.2 | 90 | 10 | 1000 | 0.1 | 0.9 | 2 | 216 | 0.2 | 21.6 |
| 31 | 2.5 | -0.2 | 90 | 10 | 1000 | 0.125 | 0.9 | 2 | 270 | 0.3125 | 33.75 |
| 32 | 3 | -0.2 | 90 | 10 | 1000 | 0.15 | 0.9 | 2 | 324 | 0.45 | 48.6 |
| 33 | 1 | -0.1 | 95 | 5 | 1000 | 0.05 | 0.95 | 2 | 114 | 0.05 | 5.7 |
| 34 | 2 | -0.1 | 95 | 5 | 1000 | 0.1 | 0.95 | 2 | 228 | 0.2 | 22.8 |
| 35 | 2.5 | -0.1 | 95 | 5 | 1000 | 0.125 | 0.95 | 2 | 285 | 0.3125 | 35.625 |
| 36 | 3 | -0.1 | 95 | 5 | 1000 | 0.15 | 0.95 | 2 | 342 | 0.45 | 51.3 |
| 37 | 1 | -0.2 | 95 | 5 | 1000 | 0.05 | 0.95 | 2 | 114 | 0.05 | 5.7 |
| 38 | 2 | -0.2 | 95 | 5 | 1000 | 0.1 | 0.95 | 2 | 228 | 0.2 | 22.8 |
| 39 | 2.5 | -0.2 | 95 | 5 | 1000 | 0.125 | 0.95 | 2 | 285 | 0.3125 | 35.625 |
| 40 | 3 | -0.2 | 95 | 5 | 1000 | 0.15 | 0.95 | 2 | 342 | 0.45 | 51.3 |
| 41 | 1 | -0.2 | 75 | 25 | 100 | 0.05 | 7.5 | 3 | 135 | 0.05 | 6.75 |
| 42 | 2 | -0.2 | 75 | 25 | 100 | 0.1 | 7.5 | 4 | 360 | 0.2 | 36 |
| 43 | 2.5 | -0.2 | 75 | 25 | 100 | 0.125 | 7.5 | 5 | 562.5 | 0.3125 | 70.3125 |
| 44 | 3 | -0.2 | 75 | 25 | 100 | 0.15 | 7.5 | 6 | 810 | 0.45 | 121.5 |
| 45 | 1 | -0.2 | 75 | 25 | 10000 | 0.05 | 0.075 | 7 | 315 | 0.05 | 15.75 |
| 46 | 2 | -0.2 | 75 | 25 | 10000 | 0.1 | 0.075 | 8 | 720 | 0.2 | 72 |
| 47 | 2.5 | -0.2 | 75 | 25 | 10000 | 0.125 | 0.075 | 9 | 1012.5 | 0.3125 | 126.5625 |
| 48 | 3 | -0.2 | 75 | 25 | 10000 | 0.15 | 0.075 | 10 | 1350 | 0.45 | 202.5 |

FIG. 6B

ELECTRICAL SIGNALS FOR RETRIEVAL OF MATERIAL FROM VESSEL LUMENS

TECHNICAL FIELD

The present technology relates generally to devices, systems, and methods for removing obstructions from body lumens. Some embodiments of the present technology relate to devices and methods for delivering electrical signals within a medical treatment system.

BACKGROUND

Many medical procedures use medical devices to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments may increase the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e., clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (e.g., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there may be complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that may contribute to clot release during retrieval include: (a) boundary conditions at bifurcations; (b) changes in vessel diameter; and/or (c) vessel tortuosity, amongst others.

Certain blood components, such as platelets and coagulation proteins, display negative electrical charges. In some embodiments, the treatment systems of the present technology include an interventional element and a signal generator configured to positively charge at least a portion of the interventional element during one or more stages of a thrombectomy procedure. For example, the signal generator can apply an electrical signal to the interventional element in a manner that positively charges the interventional element. The positively charged interventional element can attract negatively charged blood components, thereby improving attachment of the thrombus to the interventional element and reducing the number of device passes or attempts necessary to fully retrieve the clot.

In some embodiments, the treatment system includes an elongate core assembly extending between the signal generator and the interventional element. The interventional element and/or a component of the core assembly can serve as a first electrode, and the treatment system can further include a second electrode that may be disposed at a number of different locations. For example, the second electrode can be a component of the core assembly, such as a conductive element coupled to or integrated within the core assembly. Additionally or alternatively, the second electrode can take the form of a needle, a grounding pad, a conductive element carried by one or more catheters of the treatment system, a separate guide wire, and/or any other suitable conductive element configured to complete an electrical circuit with the first electrode and the extracorporeally positioned signal generator. When the interventional element is placed in the presence of blood (or any other electrolytic medium), current can travel from a first terminal of the signal generator to the core assembly and the interventional element, through the blood, to the second electrode, and back to a second terminal of the signal generator, thereby positively charging at least a portion of the interventional element and adhering clot material thereto.

While applying an electrical signal to positively charge the thrombectomy device can improve attachment of the thrombus to the retrieval device, certain waveforms and power delivery parameters may be particularly effective for promoting thrombus attachment. In some embodiments, it is important to provide sufficient current and power to enhance clot-adhesion without ablating tissue or generating new clots (i.e., the delivered power should not be significantly thrombogenic) or causing the creation of bubbles or gas on the surface of the interventional element. The clot-adhesion effect appears to be driven by the peak current of the delivered electrical signal. In some embodiments, periodic waveforms may advantageously provide the desired peak current without delivering excessive total energy. In particular, providing a periodic waveform with intermittent polarity reversal (e.g., a predominantly positive waveform that includes periods of intermittent negative polarity) can provide effective clot adhesion while reducing the risk of new clot formation or bubble formation on the interventional element. For example, in some embodiments, a waveform can alternate between positive peaks (e.g., of around 2 mA) that deliver positive electrical charge to the interventional element and slightly negative troughs (e.g., of around −0.2 mA) interspersed between the positive peaks. In some instances, the negative troughs have been found to reduce adverse events such as new clot formation and gas formation on the interventional element while still allowing for enhanced clot adhesion.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The present technology is illustrated, for example, according to various aspects described below. These are provided as examples and do not limit the present technology.

In one aspect of the present technology, a system for removing a thrombus is provided. The system can include an interventional element configured to be disposed proximate to or adjacent to a thrombus within a blood vessel, and a signal generator in electrical communication with the interventional element. The signal generator can be configured to deliver an electrical signal to the interventional element. The electrical signal can include a waveform having a positive phase having a peak positive current and a first duration, and a negative phase having a peak negative current and a second duration. A magnitude of the peak positive current can be greater than a magnitude of the peak negative current, and the first duration can be greater than the second duration.

In some embodiments, the first duration is at least 99%, 95%, 90%, 85%, 80%, 75%, or 70% of a period of the waveform. The second duration can be no more than 30%, 25%, 20%, 15%, 10%, 5%, or 1% of a period of the waveform. The magnitude of the peak positive current can be at least 2 times, 3 times, 4 times, 5 times, 6 times, 7 times, 8 times, 9 times, or 10 times greater than the magnitude of the peak negative current. The peak positive current can be within a range from 1 mA to 5 mA. The peak negative current can be within a range from −0.01 mA to −0.5 mA.

In some embodiments, the waveform has a frequency within a range from 100 Hz to 10 kHz. The waveform can include a square waveform, a triangular waveform, a sawtooth waveform, a trapezoidal waveform, a sinusoidal waveform, or a combination thereof. Optionally, the positive phase can include a plurality of repeated pulses. The plurality of repeated pulses can include a plurality of square pulses, triangular pulses, sawtooth pulses, trapezoidal pulses, sinusoidal pulses, or a combination thereof. In some embodiments, the positive phase includes two to ten repeated pulses.

In some embodiments, the interventional element includes a self-expanding mesh structure. Optionally, the system can further include a core assembly. The core assembly can include a first conductor coupled to the interventional element, and a second conductor extending distally from the first conductor. The signal generator can be configured to deliver the electrical signal to the first and second conductors. The second conductor can include a distal tip having a linear, curved, hooked, helical, spiral, spherical, or spheroidal shape.

In another aspect of the present technology, a method for removing a thrombus is provided. The method can include applying a periodic electrical signal to an interventional element positioned near a thrombus in a blood vessel. The periodic electrical signal can include a positive signal portion having a peak positive current, and a negative signal portion having a peak negative current. The peak positive current can have a greater magnitude than the peak negative current, and the positive signal portion can have a greater duty cycle than the negative signal portion.

In some embodiments, the positive signal portion has a duty cycle greater than or equal to 99%, 95%, 90%, 85%, 80%, 75%, or 70%. The negative signal portion can have a duty cycle less than or equal to 30%, 25%, 20%, 15%, 10%, 5%, or 1%. The peak positive current can have a magnitude at least 2 times, 3 times, 4 times, 5 times, 6 times, 7 times, 8 times, 9 times, or 10 times greater than a magnitude of the peak negative current.

In some embodiments, the periodic electrical signal is applied for no more than 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1.5 minutes, 1 minute, or 30 seconds. The periodic electrical signal can be applied during a single session having a duration of no more than 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1.5 minutes, 1 minute, or 30 seconds. Alternatively, the periodic electrical signal can be applied during a plurality of sessions, each session having a duration of no more than 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1.5 minutes, 1 minute, or 30 seconds. The plurality of sessions can include 2 sessions, 3 sessions, 4 sessions, 5 sessions, 6 sessions, 7 sessions, 8 sessions, 9 sessions, or 10 sessions. The sessions can be spaced apart by at least 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1.5 minutes, 1 minute, or 30 seconds.

In some embodiments, the interventional element forms a first electrode, and the method further includes applying the periodic electrical signal to at least one second electrode spaced apart from the first electrode. The at least one second electrode can be located on a conductive element positioned in the blood vessel and spaced apart from the interventional element. Optionally, the conductive element can include a main body and a distal tip connected to the main body, the distal tip forming the second electrode. In some embodiments, the at least one second electrode includes at least one external electrode. Optionally, the method can further include generating a positive charge on the interventional element with the periodic electrical signal.

In a further aspect of the present technology, a method for removing a thrombus from a patient is provided. The method can include positioning an interventional element near or adjacent to a thrombus within a blood vessel. The method can also include promoting adhesion of the thrombus to the interventional element by delivering an electrical signal to the interventional element. The electrical signal can have a waveform including a positive phase and a negative phase. The positive and negative phases can be asymmetric so as to positively charge at least a portion of the interventional element.

In some embodiments, the positive phase has a first pulse width, and the negative phase has a second pulse width shorter than the first pulse width. Optionally, the positive phase can have a first amplitude, and the negative phase can have a second amplitude smaller than the first amplitude. The waveform can have a frequency within a range from 100 Hz to 10 kHz.

In some embodiments, the method further includes delivering the electrical signal to one or more electrodes spaced apart from the interventional element. The one or more electrodes can include a conductive element positioned distal to the interventional element. The one or more electrodes can include an electrode external to the patient's body.

Additional features and advantages of the present technology will be set forth in the description below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 6A and 6B are tables of example waveform characteristics and power delivery parameters, in accordance with one or more embodiments of the present technology.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments, in addition to those described herein, are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.). In some embodiments, aspects of the present technology can be applied to medical devices and systems that are not configured for removal of material from vessel lumens, for example, systems and devices for neuromodulation, or any other suitable medical procedure.

Figure 1A:
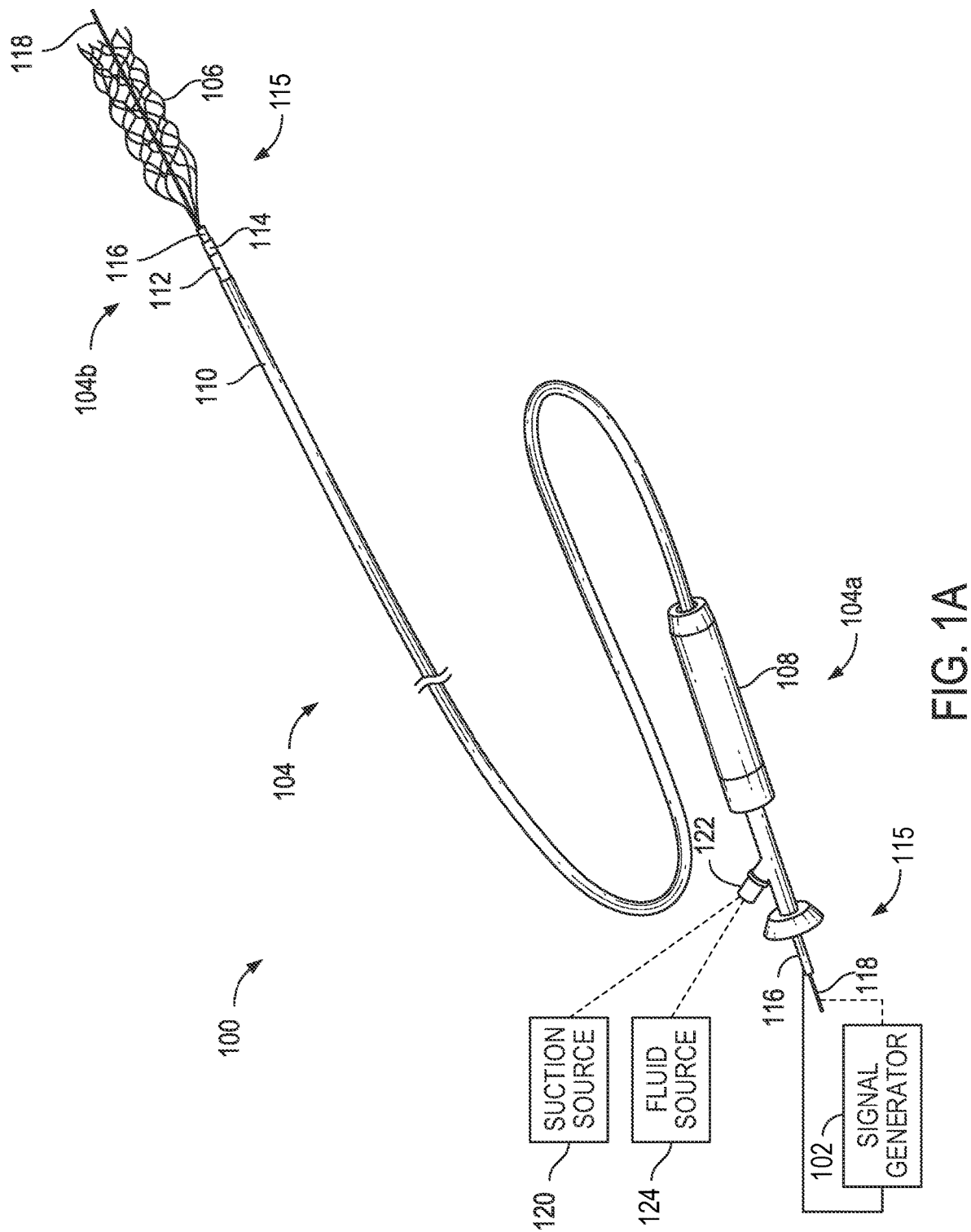
FIG. 1A shows a perspective view of an electrically enhanced treatment system for retrieving material from a body lumen, in accordance with one or more embodiments of the present technology.

FIGS. 1A-1F illustrate an electrically enhanced treatment system 100 according to one or more embodiments of the present technology. Specifically, FIG. 1A is a perspective view of the treatment system 100 and FIGS. 1B-1F illustrate various components of the treatment system 100. Referring first to FIG. 1A, the treatment system 100 includes a signal generator 102 and a treatment device 104. The treatment device 104 includes a proximal portion 104a configured to be coupled to the signal generator 102 and a distal portion 104b configured to be intravascularly positioned within a blood vessel (such as an intracranial blood vessel) at a treatment site at or proximate a thrombus. The treatment device 104 includes an interventional element 106 at the distal portion 104b, a handle 108 at the proximal portion 104a, and a plurality of elongated shafts or members extending therebetween. For example, in the illustrated embodiment, the treatment device 104 includes a first catheter 110 (such as a guide catheter or balloon guide catheter), a second catheter 112 (such as a distal access catheter or aspiration catheter) configured to be slidably disposed within a lumen of the first catheter 110, a third catheter 114 (such as a microcatheter) configured to be slidably disposed within a lumen of the second catheter 112, and a core assembly 115 configured to be slidably disposed within a lumen of the third catheter 114. In other embodiments, however, the treatment device 104 may not include some of the components shown in FIG. 1A, such as the first catheter 110 and/or the second catheter 112.

The interventional element 106 can be or include any suitable device for restoring blood flow in a patient's vasculature (e.g., cerebral vasculature), such as a clot removal device, a thrombectomy device, or other suitable medical device. For example, the interventional element 106 can be a stent and/or stent retriever, such as Medtronic's Solitaire™ Revascularization Device, Stryker Neurovascular's Trevo® ProVue™ Stentriever, or other suitable devices. In some embodiments, the interventional element 106 is or includes a coiled wire, a weave, and/or a braid formed of a plurality of braided filaments. Examples of suitable interventional elements 106 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 106 can be configured in many ways. For example, the interventional element 106 can have a low-profile, constrained, and/or compressed configuration for intravascular delivery to the treatment site within the treatment device 104, such as within the third catheter 114, and an expanded configuration for securing and/or engaging clot material and/or for restoring blood flow at the treatment site. In some embodiments, the interventional element 106 is or includes a mesh structure (e.g., a braid, a stent, etc.) formed of a superelastic material (e.g., nitinol) or other resilient or self-expanding material configured to self-expand when released from the third catheter 114. The mesh structure can include a plurality of struts and open spaces between the struts. In some embodiments, the struts and spaces may be situated along the longitudinal direction of the interventional element 106, the radial direction, or both.

The interventional element 106 can be coupled to a distal portion of the core assembly 115. The core assembly 115 can be an elongated structure extending between the proximal portion 104a and distal portion 104b of the treatment device 104. In the illustrated embodiment, for example, the core assembly 115 includes a first conductor 116 and a second conductor 118. The first conductor 116 can be a first elongate member (e.g., a wire, tube (such as a hypotube), coil, rod, shaft, or any combination thereof) configured to advance the interventional element 106 to a treatment site within a blood vessel. The second conductor 118 can be a second elongate member (e.g., a wire, tube (such as a hypotube), coil, rod, shaft, or any combination thereof) configured to secure or retain a position of the interventional element 106 relative to the first conductor 116, and electrically isolated from the first conductor 116. In some embodiments, the first conductor 116 is an elongate tubular member defining a lumen therethrough, and the second conductor 118 is disposed within and extends through the lumen of the first conductor 116. The first conductor 116 and second conductor 118 can be coaxial. The first conductor 116 and second conductor 118 can be slidably or non-slidably coupled together.

The first conductor 116 and second conductor 118 can be sized and configured to be advanced through a corporeal lumen to a treatment site within the patient's body. For example, the first and second conductors 116, 118 can each have a length sufficient to extend from a location outside the patient's body, through the vasculature, and proximate a thrombus within a lumen of a blood vessel, such as within a patient's neurovasculature. In some embodiments, the first and second conductors 116, 118 are conductive elements for transmitting electrical signals during the treatment procedure. Additional features of the first conductor 116 and second conductor 118 are described in greater detail below with respect to FIGS. 1D-1F.

The core assembly 115 can be slidably disposed within the lumen of the third catheter 114. The third catheter 114 can be generally constructed to track over a conventional guidewire in the cervical anatomy and into the cerebral vessels associated with the brain, and can also be chosen according to several standard designs that are generally available. For example, the third catheter 114 can have a length of at least 125 cm, and more particularly may have a length within a range from about 125 cm to about 175 cm long. Other designs and dimensions are also contemplated. The second catheter 112 can be configured to slidably receive the third catheter 114 therethrough. The first catheter 110 can be configured to slidably receive both the second catheter 112 and the third catheter 114 therethrough. In some embodiments, the first catheter 110 is a balloon guide catheter having an inflatable balloon or other expandable member surrounding the catheter shaft at or near its distal end. Alternatively, the first catheter 110 can be a guide catheter without a balloon. The first catheter 110 can optionally be coupled to or incorporate the handle 108.

In some embodiments, the catheters 110, 112, and 114 are each formed as a generally tubular member extending along and about a central axis. The bodies of the catheters 110, 112, and/or 114 can be made from various materials, such as thermoplastics, e.g., polytetrafluoroethylene (PTFE or TEFLON®), fluorinated ethylene propylene (FEP), high-density polyethylene (HDPE), polyether ether ketone (PEEK), etc. Optionally, the inner and/or outer surfaces of any of the catheters 110, 112, and 114 can be coated with one or more materials, depending on the desired results. For example, the inner and/or outer surfaces can be lined with a hydrophilic material such as polyvinylpyrrolidone (PVP) or some other plastic coating.

In some embodiments, the treatment system 100 includes a suction source 120 (e.g., a syringe, a pump, etc.) configured to be fluidically coupled (e.g., via a connector 122) to a proximal portion of one or more of the first catheter 110, the second catheter 112, and/or the third catheter 114 to apply negative pressure therethrough. For example, a proximal portion of the second catheter 112 can be coupled to the suction source 120 in order to supply negative pressure to a treatment site. The treatment system 100 can optionally include a fluid source 124 (e.g., a fluid reservoir, a syringe, pump, etc.) configured to be fluidically coupled (e.g., via the connector 122 or a different connector) to a proximal portion of one or more of the first catheter 110, the second catheter 112, and/or the third catheter 114 to supply fluid (e.g., saline, contrast agents, a drug such as a thrombolytic agent, etc.) to the treatment site.

In some embodiments, the signal generator 102 is configured to deliver an electrical signal (e.g., an electrical current) to one or more portions of the treatment device 104 to enhance thrombus engagement and/or removal. For example, the signal generator 102 can be electrically coupled to the interventional element 106 to deliver electrical current thereto, e.g., to positively charge at least a portion of the interventional element 106 to attract negatively-charged blood components and/or otherwise improve attachment of clot material to the interventional element 106. The interventional element 106 can be an electrically conductive thrombectomy device that includes and/or is made of a metallic and/or electrically conductive material, such as stainless steel, nitinol, cobalt-chromium, platinum, tantalum, alloys thereof, or any other suitable material.

The signal generator 102 can be coupled to a proximal portion of the core assembly 115, the third catheter 114, the second catheter 112, and/or first catheter 110 to provide electric signals to the interventional element 106. For example, in the illustrated embodiment, the signal generator 102 is coupled to the core assembly 115 (e.g., to the first conductor 116, the second conductor 118, or both) to deliver electrical signals to the interventional element 106 and thereby provide an electrically charged environment at the distal portion 104b of the treatment device 104. The coupling between the signal generator 102 and the core assembly 115 can also provide a conductive pathway for electrical current to return from the electrically charged environment to the signal generator 102. For example, in some embodiments, when the interventional element 106 is placed in the presence of blood (or thrombus, and/or any other electrolytic medium which may be present, such as saline) and voltage is applied via the electrical connectors of the signal generator 102, current flows from the signal generator 102, along the first conductor 116 to the interventional element 106 and through the surrounding media (e.g., blood, tissue, thrombus, etc.), returning proximally along the second conductor 118 to the signal generator 102, thereby positively charging at least a portion of the interventional element 106 and promoting clot adhesion.

Figure 1B:
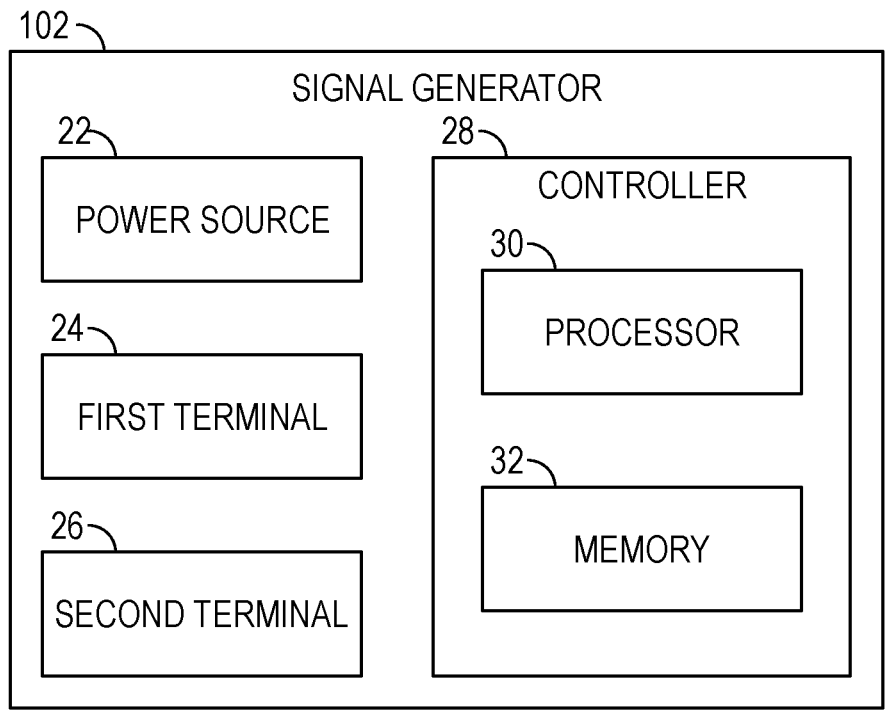
FIG. 1B shows a schematic view of a signal generator of the treatment system of FIG. 1A, in accordance with one or more embodiments of the present technology.
Figure 1C:
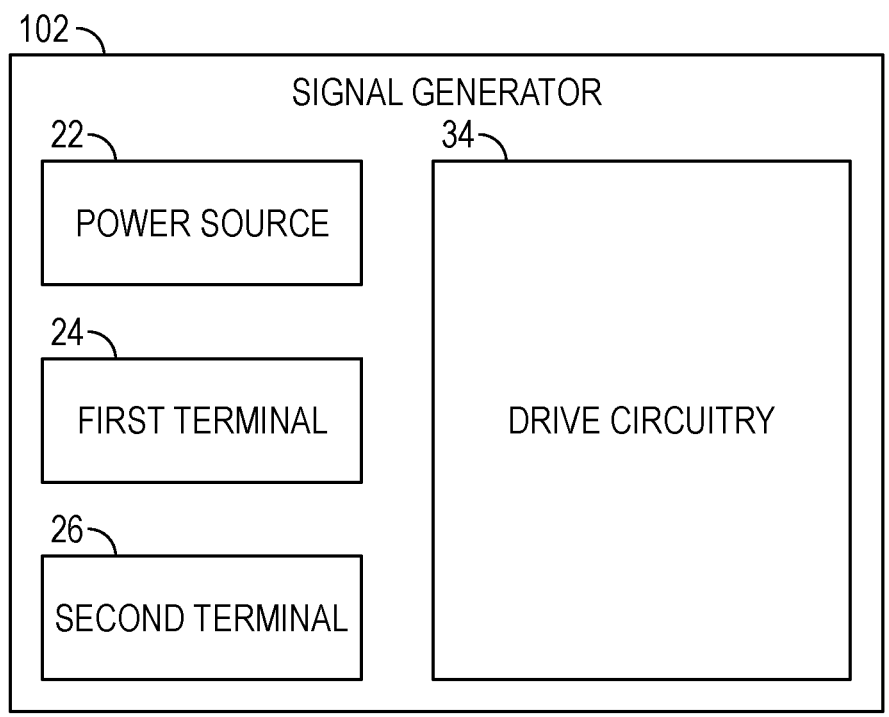
FIG. 1C shows a schematic view of a signal generator of the treatment system of FIG. 1A, in accordance with one or more embodiments of the present technology.

FIGS. 1B and 1C are schematic views of different embodiments of the signal generator 102. With reference to FIG. 1B, the signal generator 102 can include a power source 22, a first terminal 24, a second terminal 26, and a controller 28. The first and second terminals 24, 26 can be connectors, electrodes, etc., for electrically coupling the signal generator 102 to another component of the treatment system 100, such as to the core assembly 115. For example, the first terminal 24 can be electrically coupled to the first conductor 116, and the second terminal 26 can be electrically coupled to the second conductor 118, or vice-versa. The controller 28 includes a processor 30 coupled to a memory 32 that stores instructions (e.g., in the form of software, code or program instructions executable by the processor or controller) for causing the power source 22 to deliver electrical signals according to certain parameters provided by the software, code, etc. The controller 28 can be used to control various parameters of the energy output by the power source or generator, such as waveform, intensity, amplitude, duration, frequency, duty cycle, and/or polarity. For example, the signal generator 102 can provide a voltage within a range from about 2 volts to about 28 volts (positive or negative) and a current within a range from about 0.5 mA to about 20 mA (positive or negative). The power source 22 of the signal generator 102 may include a DC power supply, an AC power supply, and/or a power supply switchable between DC and AC.

FIG. 1C illustrates another embodiment of the signal generator 102, in which the controller 28 of FIG. 1B is replaced with drive circuitry 34. In this embodiment, the signal generator 102 can include hardwired circuit elements to provide the desired waveform delivery, rather than the software-based generator of FIG. 1B. The drive circuitry 34 can include, for example, analog circuit elements (e.g., resistors, diodes, switches, etc.) that are configured to cause the power source 22 to deliver electrical current via the first and second terminals 24, 26 according to the desired parameters. For example, the drive circuitry 34 can be configured to cause the power source 22 to deliver periodic waveforms via the first and second terminals 24, 26.

Figure 1D:
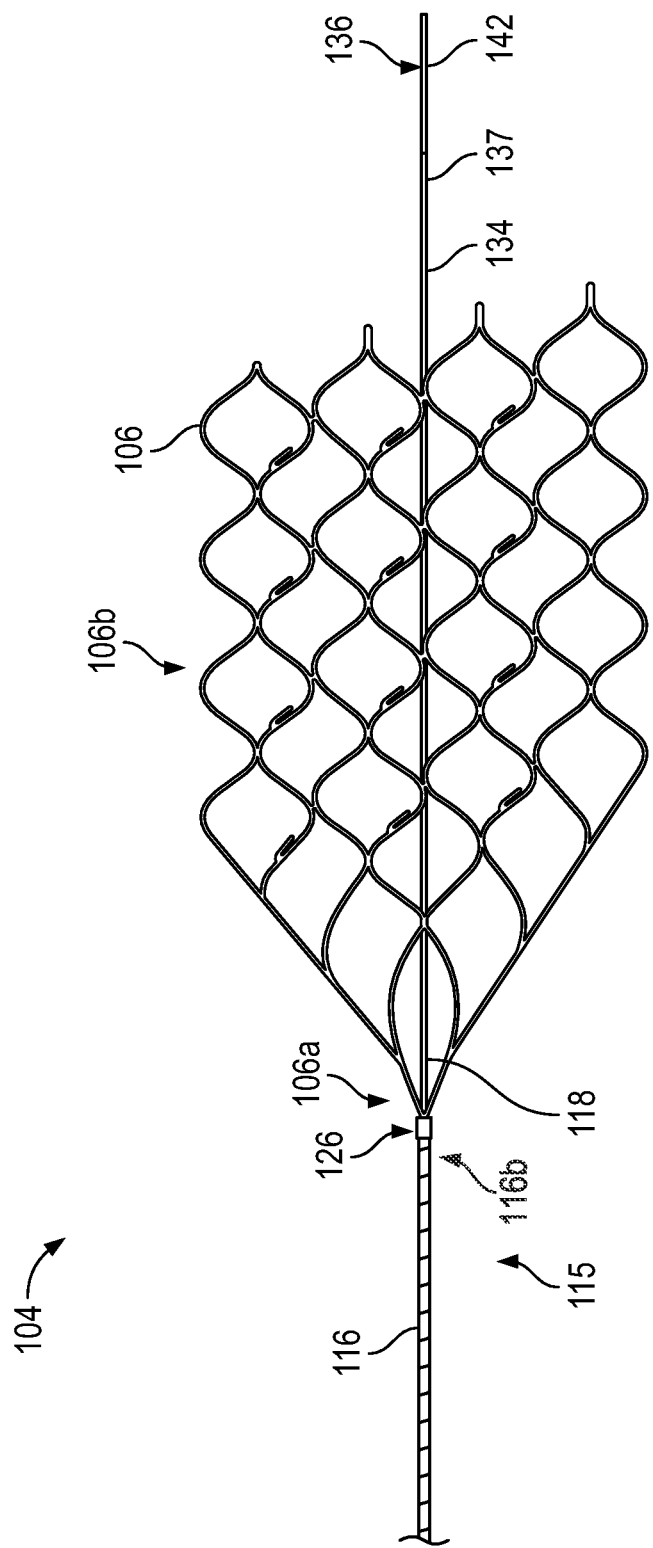
FIG. 1D shows a side view of a portion of the treatment device of the treatment system of FIG. 1A, in accordance with one or more embodiments of the present technology.
Figure 1E:
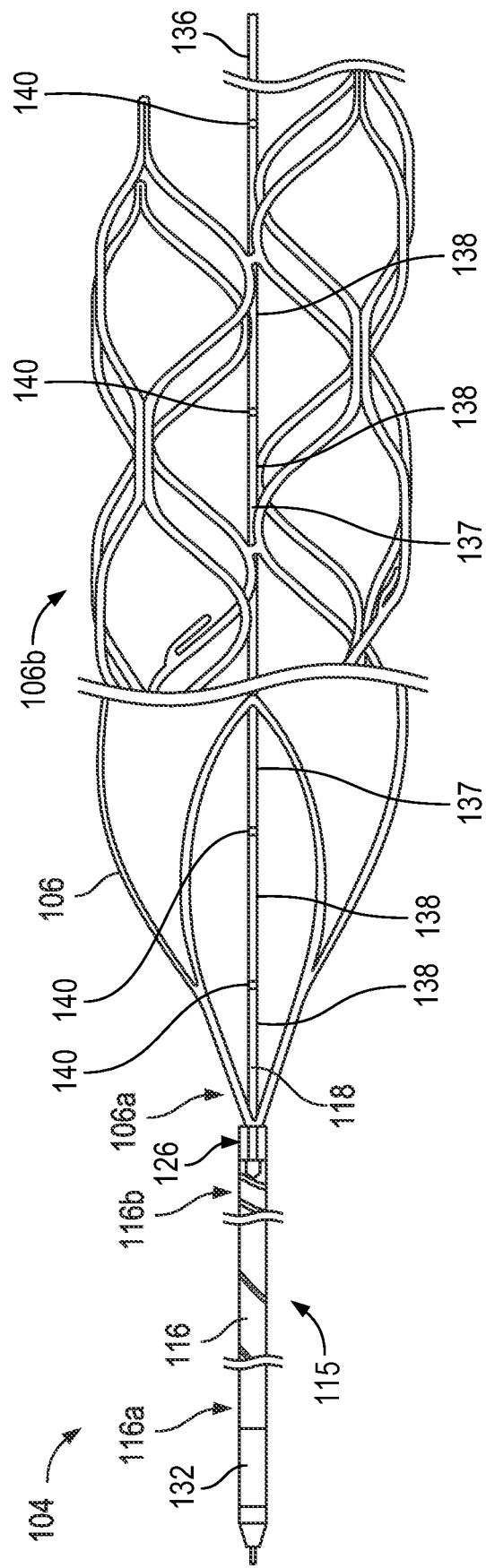
FIG. 1E shows an enlarged side view of a portion of the treatment device of the treatment system of FIG. 1A, in accordance with one or more embodiments of the present technology.

FIGS. 1D and 1E are side views of the treatment device 104 including the interventional element 106 and core assembly 115 (FIG. 1D shows the interventional element 106 in an unrolled and/or flattened state, and FIG. 1E shows the interventional element 106 in a rolled and/or coiled state). As illustrated in FIGS. 1D and 1E, the interventional element 106 has a proximal portion including an attachment portion 106a that can be coupled to the first conductor 116, and a distal portion including an open cell framework or body 106b. When in the rolled and/or coiled state, the body 106b of the interventional element 106 can be generally tubular (e.g., cylindrical—best seen in FIG. 1E), and the proximal portion of the interventional element 106 can taper proximally to form the attachment portion 106a.

In some embodiments, the interventional element 106 is coupled to a distal portion 116b of the first conductor 116 and extends distally beyond the first conductor 116. The first conductor 116 and the interventional element 106 can be coupled at a connection 126 to secure the interventional element 106 relative to the first conductor 116 and/or to complete an electrical pathway between the first conductor 116 and the interventional element 106, as described in greater detail below. The second conductor 118 can extend through the lumen of the first conductor 116 and distally beyond the first conductor 116, such that a distal portion of the second conductor 118 extends through and/or beyond an interior region of the interventional element 106 (best seen in FIG. 1E).

The first conductor 116 can be a monolithic structure or can be formed of multiple joined segments. In some embodiments, the first conductor 116 is or includes a laser-cut hypotube having a spiral cut pattern (or other pattern of cut voids) formed in its sidewall along at least a portion of its length. The first conductor 116 can be metallic and/or otherwise electrically conductive to deliver electrical signals from the signal generator 102 to the interventional element 106. For example, the first conductor 116 can include or consist of nickel titanium alloy, stainless steel, or other metals or alloys. In embodiments where the first conductor 116 includes multiple joined segments, the segments may be formed of the same or different materials. For example, some or all of the first conductor 116 can be formed of stainless steel, or other suitable materials known to those skilled in the art. Nickel titanium alloy may be preferable for kink resistance and reduction of imaging artifacts.

The second conductor 118 can be a monolithic structure or can be formed of multiple joined segments. The second conductor 118 can be metallic and/or otherwise electrically conductive to deliver electrical signals from the signal generator 102 to the surrounding media (e.g., blood, tissue, thrombus, etc.). For example, the second conductor 118 can include or consist of nickel titanium alloy, stainless steel, or other metals or alloys. In embodiments where the second conductor 118 includes multiple joined segments, the segments may be formed of the same or different materials. For example, some or all of the second conductor 118 can be formed of stainless steel, or other suitable materials known to those skilled in the art. Nickel titanium alloy may be preferable for kink resistance and reduction of imaging artifacts.

Figure 1F:
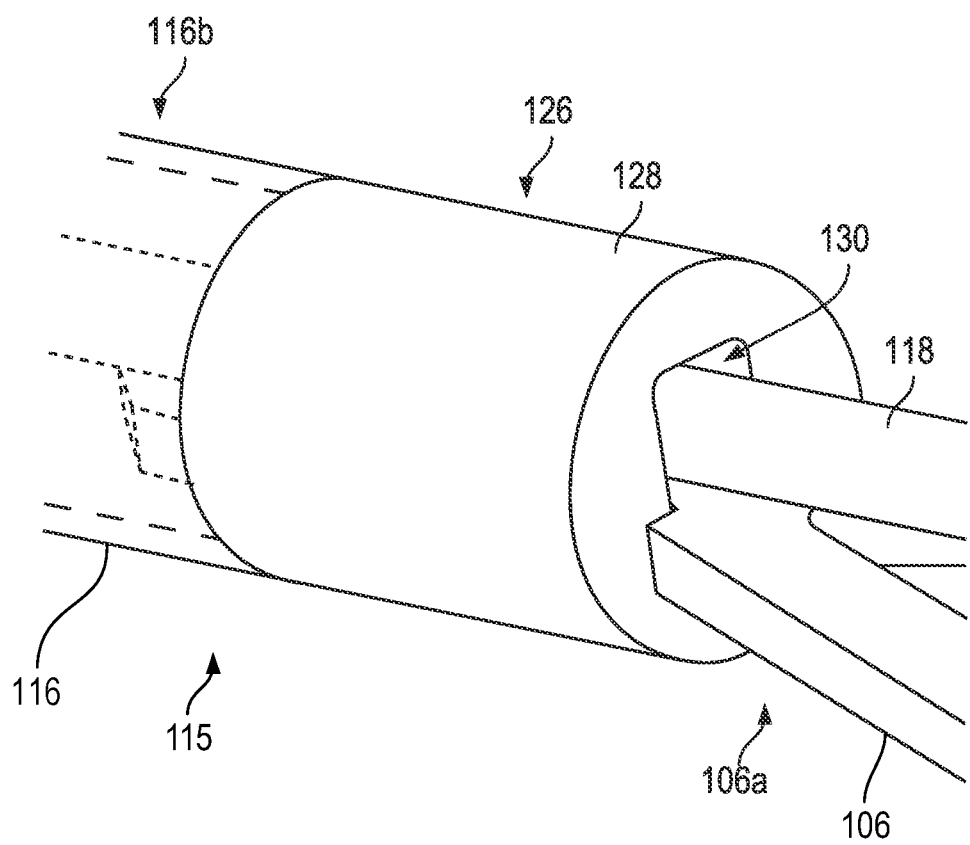
FIG. 1F shows an enlarged perspective view of a connection between a first conductor and an interventional element of the treatment system of FIG. 1A, in accordance with one or more embodiments of the present technology.

FIG. 1F illustrates an enlarged perspective view of the connection 126 between the first conductor 116 and the interventional element 106. In some embodiments, the interventional element 106 and the first conductor 116 are substantially permanently attached together at the connection 126 such that, under the expected use conditions of the treatment device 104, the interventional element 106 and the first conductor 116 will not become unintentionally separated from one another. In some embodiments, the treatment device 104 includes a portion (e.g., located proximally or distally of the connection 126) that is configured for selective detachment of the interventional element 106 from the first conductor 116. For example, such a portion can comprise an electrolytically severable segment of the first conductor 116. In other embodiments, however, the treatment device 104 can be devoid of any feature that would permit selective detachment of the interventional element 106 from the first conductor 116.

In some embodiments, the first conductor 116 includes a distally located joining element 128 including an aperture 130 configured to receive the attachment portion 106a of the interventional element 106 and/or at least a portion of the second conductor 118. The attachment portion 106a of the interventional element 106 can be configured to mechanically interlock with the joining element 128 to secure the interventional element 106 to the core assembly 115. In some embodiments, the second conductor 118 is disposed within the aperture 130, e.g., at a radially adjacent position relative to the attachment portion 106a, to facilitate such securement. Further, the second conductor 118 may be affixed to the joining element 128 via a weld, an adhesive, a threaded connection, an interference fit, or any other suitable connection.

Optionally, the connection 126 can include a bonding agent, in addition or alternatively to the joining element 128 and/or second conductor 118. The bonding agent can be or include an adhesive, solder, welding flux, brazing filler, etc., disposed within the joining element 128 (e.g., within the aperture 130), adjacent to the joining element 128, proximal to the joining element 128, and/or distal of the joining element 128. In some embodiments, the bonding agent bonds to the other components of the connection 126 (e.g., to the first conductor 116, attachment portion 106a, joining element 128, and/or second conductor 118) without applying heat. For example, the bonding agent can be or include a UV-curable adhesive. In embodiments where the other components of the connection 126 include polymeric materials (e.g., a polymer coating on the first and/or second conductors 116, 118; polymer tubing) use of a bonding agent that avoids application of heat that would damage the polymer may be preferred.

Referring again to FIGS. 1D and 1E together, the treatment device 104 can comprise one or more electrically insulating materials, such as a polymer (e.g., polyimide, Parylene, or PTFE). For example, the first conductor 116 and/or the second conductor 118 can be electrically insulated along at least a portion of their respective lengths, e.g., to prevent electrical shorting. An insulating material can be disposed along an entire length of the first conductor 116 and/or the second conductor 118, or the insulating material can be disposed along select portions of the first conductor 116 and/or the second conductor 118. Moreover, an insulating material can be disposed over an outer surface of the interventional element 106 and/or along at least a portion of the length of the interventional element 106.

For example, as shown in FIG. 1E, an insulating material 132 can be disposed over an outer surface of the first conductor 116 and/or along at least a portion of a length of the first conductor 116, e.g., to direct current through the first conductor 116 and prevent current loss from the first conductor 116 to the surrounding environment. In the illustrated embodiment, the insulating material 132 is disposed near or adjacent to a proximal portion 116a of the first conductor 116. Alternatively or in combination, the insulating material 132 can be disposed near or adjacent to a distal portion 116b of the first conductor 116, and/or at select locations along the length of the first conductor 116 between the proximal and distal portions 116a, 116b. Optionally, the insulating material 132 can be disposed within a lumen of the first conductor 116 to electrically isolate the first conductor 116 from the second conductor 118 and/or the attachment portion 106a of the interventional element 106.

As another example, as shown in FIG. 1D, an insulating material 134 can be disposed on one or more portions of the second conductor 118, e.g., to electrically isolate the second conductor 118 from the first conductor 116, the connection 126, and/or the interventional element 106. Alternatively or in combination, the insulating material 134 can be used to define one or more individual electrodes along the length of the second conductor 118. In such embodiments, the insulating material 134 can be disposed at selected locations of the second conductor 118, such that the second conductor 118 includes at least one insulated portion and at least one uninsulated portion that can serve as an electrode. The uninsulated portion(s) can be exposed sections of electrically conductive material configured to conduct current to and/or from surrounding media (e.g., blood, tissue, thrombus, etc.) at a treatment site.

The number, positioning, and geometry (e.g., size, shape) of the insulated portions and uninsulated portions of the second conductor 118 can be varied as desired. In the embodiment of FIG. 1D, for example, the insulating material 134 extends only partially along the length of the second conductor 118, such that a main body 137 of the second conductor 118 is insulated while a distal tip 136 of the second conductor 118 distal to the main body 137 remains uninsulated. The distal tip 136 can also extend distally beyond the interventional element 106. In some embodiments, the distal tip 136 is configured to enable the interventional element 106 to maintain a desirable electrical charge distribution. For example, positioning the distal tip 136 distal to the interventional element 106 may encourage more current to flow through the distal portions of the interventional element 106 toward the distal tip 136, which in turn may enable the interventional element 106 to maintain a favorable electrical charge distribution (e.g., with sufficiently high charge density at the distal region of the interventional element 106, along the working length of the interventional element 106, or other suitable charge distribution). Although the distal tip 136 is illustrated as having a generally straight, linear shape, in other embodiments, the distal tip 136 can have a different shape, as described in greater detail below with respect to FIGS. 2-4.

Alternatively or in combination, the uninsulated portions can be at other locations along the second conductor 118, such as at one or more locations proximal to the distal tip 136. For example, in the embodiment of FIG. 1E, an insulating material is used to cover select regions of the main body 137 of the second conductor 118, thus forming a plurality of insulated portions 138 interspersed with a plurality of uninsulated portions 140. The insulated portions 138 can be larger than, smaller than, or have the same size as the uninsulated portions 140. Although the illustrated embodiment shows the uninsulated portions 140 as being evenly spaced along the main body 137 of the second conductor 118, in other embodiments, the uninsulated portions 140 can be spaced differently, e.g., some or all of the uninsulated portions 140 can be localized to the proximal portion of the second conductor 118, localized to the distal portion of the second conductor 118, localized to the portion of the second conductor 118 adjacent or near the interventional element 106, etc.

Referring again to FIG. 1D, some or all of the uninsulated portions of the second conductor 118 can optionally be covered with or otherwise coupled to an electrically conductive material 142. For example, the conductive material 142 can be coupled to the distal tip 136. In such embodiments, the conductive material 142 can surround the distal tip 136 along at least a portion of the length of the distal tip 136. In some embodiments, the surface area defined by the conductive material 142 coupled to the distal tip 136 is within a range from about 5% to about 50% of the surface area defined by the conductive material coupled to the interventional element 106. Coupling the conductive material 142 to the distal tip 136 can increase the electrical conductivity of the distal tip 136. The conductive material 142 can be or include a material that has a higher electrical conductivity than the material used to form the distal tip 136. For example, the conductive material 142 can be formed from a gold coating while the distal tip 136 can be formed from stainless steel. By coupling a more electrically conductive material to the distal tip, an electrical current can more easily pass through the distal tip 136 via the conductive material 142, thus increasing the electrical conductivity of the distal tip 136. In other embodiments, however, the distal tip 136 (or any of the other uninsulated portions of the second conductor 118) can be provided without the conductive material 142.

Referring again to FIG. 1A, the treatment system 100 can include multiple (e.g., two or more) distinct conductive paths or channels for delivering electrical signals. Each conductive path can be electrically coupled to a respective electrode. For example, the first conductor 116 can serve as a first conductive path and the interventional element 106 can serve as a first electrode. The second conductor 118 can serve as a second conductive path and the uninsulated portion(s) of the second conductor 118 (e.g., the distal tip 136 and/or portions 140) can serve as the second electrode (s). In other embodiments, however, the second electrode can be separate from the second conductor 118. For example, the second electrode can be carried by one or more of the third catheter 114, the second catheter 112, or first catheter 110. Alternatively or in combination, the treatment system 100 can also include one or more external electrodes that serve as the first or second electrodes, such as a needle puncturing the patient or a grounding pad applied to the patient's skin. In such embodiments, either the first conductor 116 or the second conductor 118 may be omitted from the core assembly 115. For example, the second conductor 118 can be omitted altogether, the first conductor 116 can be a solid shaft or wire without a lumen, and the second electrode can be an external component separate from the treatment device 104, such as a needle or grounding pad in contact with the patient's skin.

The signal generator 102 can be coupled to each of the conductive paths to provide electrical signals to the respective electrodes. For example, the first terminal 24 of the signal generator 102 can be coupled to the proximal portion 116a of the first conductor 116 such that the first conductor 116 functions as a first conductive path and the interventional element 106 serves as a first electrode. The second terminal 26 of the signal generator 102 can be coupled to a proximal portion of the second conductor 118 such that the second conductor 118 functions as a second conductive path and the uninsulated portion(s) of the second conductor 118 serve as a second electrode or electrodes. Optionally, the connectivity can be reversed, e.g., the first terminal 24 can be coupled to the second conductor 118 and the second terminal 26 can be coupled to the first conductor 116.

In some embodiments, the signal generator 102 is configured to deliver a DC signal, such as a constant DC signal or a pulsed DC signal. In such embodiments, the first terminal 24 can be a positive terminal, the first conductor 116 can serve as a positive conductive path, and the interventional element 106 can serve as a positive electrode. The first conductor 116 and interventional element 106 can transmit current from the signal generator 102 to the treatment site. The second terminal 26 can be a negative terminal, the second conductor 118 can serve as a negative conductive path, and the uninsulated portion(s) of the second conductor 118 can serve as a negative electrode or electrodes. The second conductor 118 and uninsulated portion(s) can therefore transmit current from the treatment site to the signal generator 102. Optionally, the polarities of the signal generator 102 can be switched, so that the negative terminal is electrically coupled to the first conductor 116 and the positive terminal is electrically coupled to the second conductor 118. This can be advantageous when, for example, attempting to attract predominantly positively charged material to the interventional element 106, or when attempting to break up a clot rather than grasp it with an interventional element 106.

Alternatively or in combination, the signal generator 102 can be configured to deliver AC signals. In certain instances, AC signals may advantageously help break apart a thrombus or other material. When the signal generator 102 is outputting an AC signal, the polarities of the first terminal 24, first conductor 116, interventional element 106, second terminal 24, second conductor 118, and uninsulated portion(s) of the second conductor 118 can vary over time. Similarly, the directionality of the current traveling through the treatment system 100 and the environment at the treatment site can also vary over time. The signal generator 102 can output any suitable type of AC signal. For example, in some embodiments, the signal generator 102 is configured to output an AC signal having a waveform that delivers a greater amount of positive current than negative current, also referred to herein as "intermittent negative polarity." A waveform with intermittent negative polarity can include positive phases having a greater peak magnitude and/or duration than the negative phases. The use of intermittent negative polarity waveforms can reduce the risk of certain adverse events such as new clot formation or bubble formation on the interventional element 106. Additional examples and features of waveforms having intermittent negative polarity are described in greater detail below.

A representative example of a method of operating the treatment system 100 will now be described. First, the treatment device 104 is positioned within a patient at a treatment site (e.g., a site of a blood clot within a vessel). The first catheter 110 can first be advanced through the vessel and then its balloon (if present) can be expanded to anchor the first catheter 110 in place and/or arrest blood flow from areas proximal of the balloon, e.g., to enhance the effectiveness of aspiration performed via the first catheter 110 and/or other catheter(s). Next, the second catheter 112 can be advanced through the first catheter 110 until the distal end of the second catheter 112 extends distally beyond the distal end of the first catheter 110. The distal end of the second catheter 112 can be positioned adjacent or proximal to the treatment site. The third catheter 114 can then be advanced through the second catheter 112 until the distal end of the third catheter 114 extends distally beyond the distal end of the second catheter 112. The interventional element 106 and core assembly 115 can then be advanced through the third catheter 114 for delivery to the treatment site.

Once the treatment device 104 is properly positioned, the user can expand the interventional element 106 so that the interventional element 106 engages with the thrombus. After the interventional element 106 engages with the thrombus, the user can couple the core assembly 115 to the signal generator 102. In some embodiments, the core assembly 115 is previously coupled to the signal generator 102. The user can interact with the signal generator 102 to deliver an electrical signal via the interventional element 106 and/or core assembly 115 (e.g., via the first conductor 116 and/or second conductor 118). As described elsewhere herein, the electrical signal can be configured to enhance engagement with the thrombus, and can be or include an AC signal, a DC signal, or combination thereof. After the electrical signal is delivered to the treatment device 104 for the desired duration, the user can interact with the signal generator 102 to stop the delivery of the electrical signal. The user can then proximally retract the treatment device 104, including the thrombus, into a surrounding catheter, and then remove the entire assembly from the patient.

The components of the treatment system 100 of FIGS. 1A-1F can be configured in many different ways. For example, the geometry (e.g., size, shape) of the distal tip 136 of the treatment device 104 can be modified to alter and/or improve the surface charge density along the surface of the second conductor 118. In some embodiments, the distal tip has structural features (e.g., curves, spiral shape, an expandable spheroid shape, etc.) that provide an enlarged surface area, e.g., compared to a straight wire or rod. This enlarged surface area may enable a more even distribution of charge density throughout the surface of the distal tip, which may reduce the risk of hydrogen and chlorine gas bubbles forming along the surface of the second conductor 118.

Figure 2:
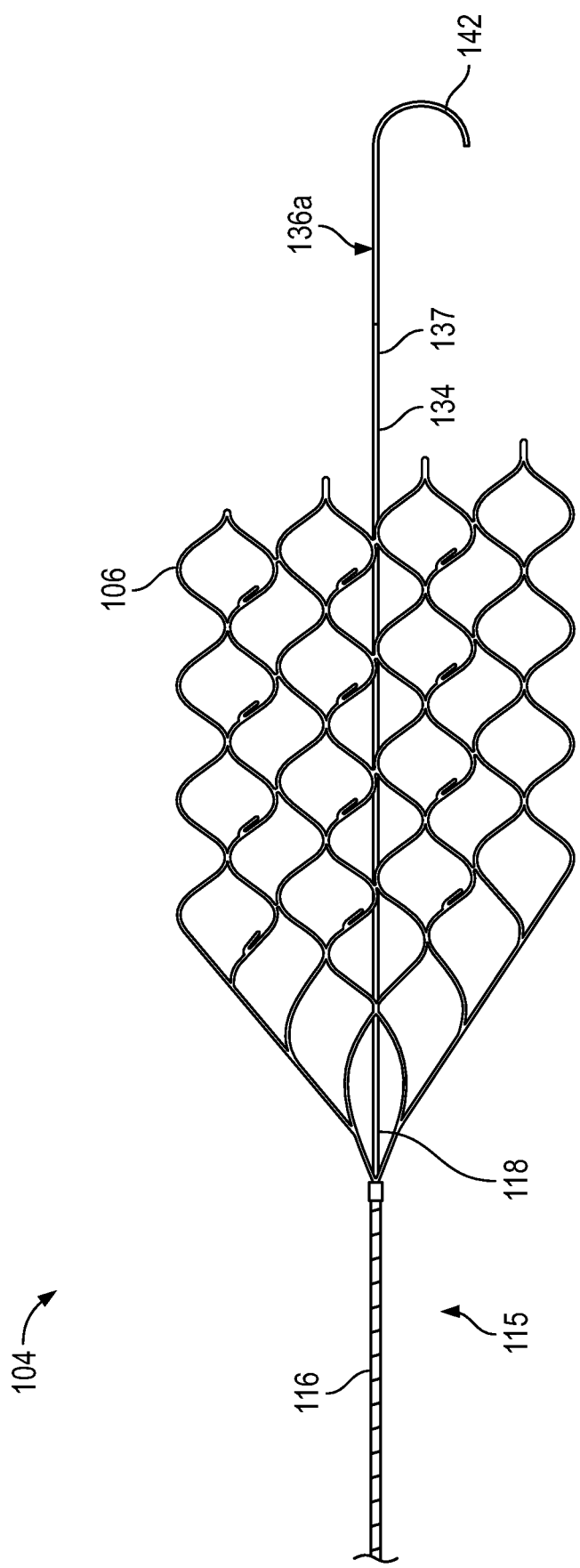
FIGS. 2-4 show side views of a portion of the treatment device of FIG. 1A with various distal tip geometries, in accordance with one or more embodiments of the present technology.
Figure 3:
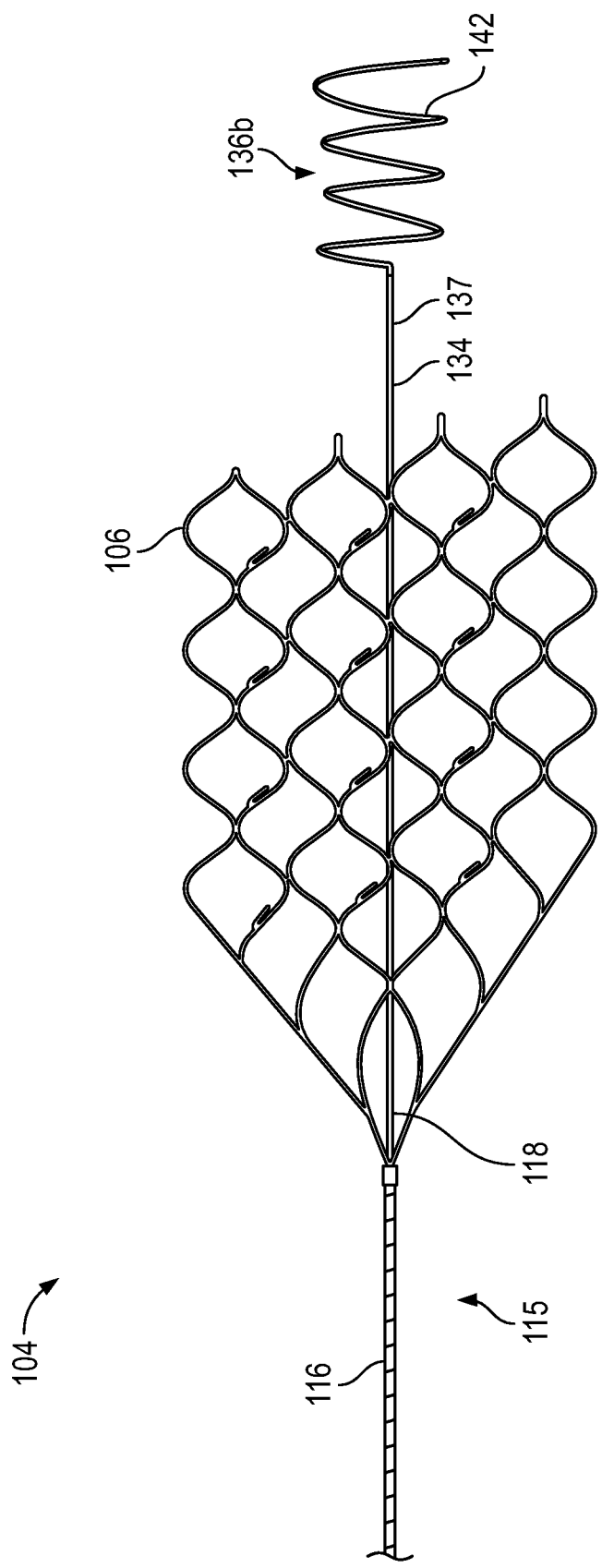
Figure 4:
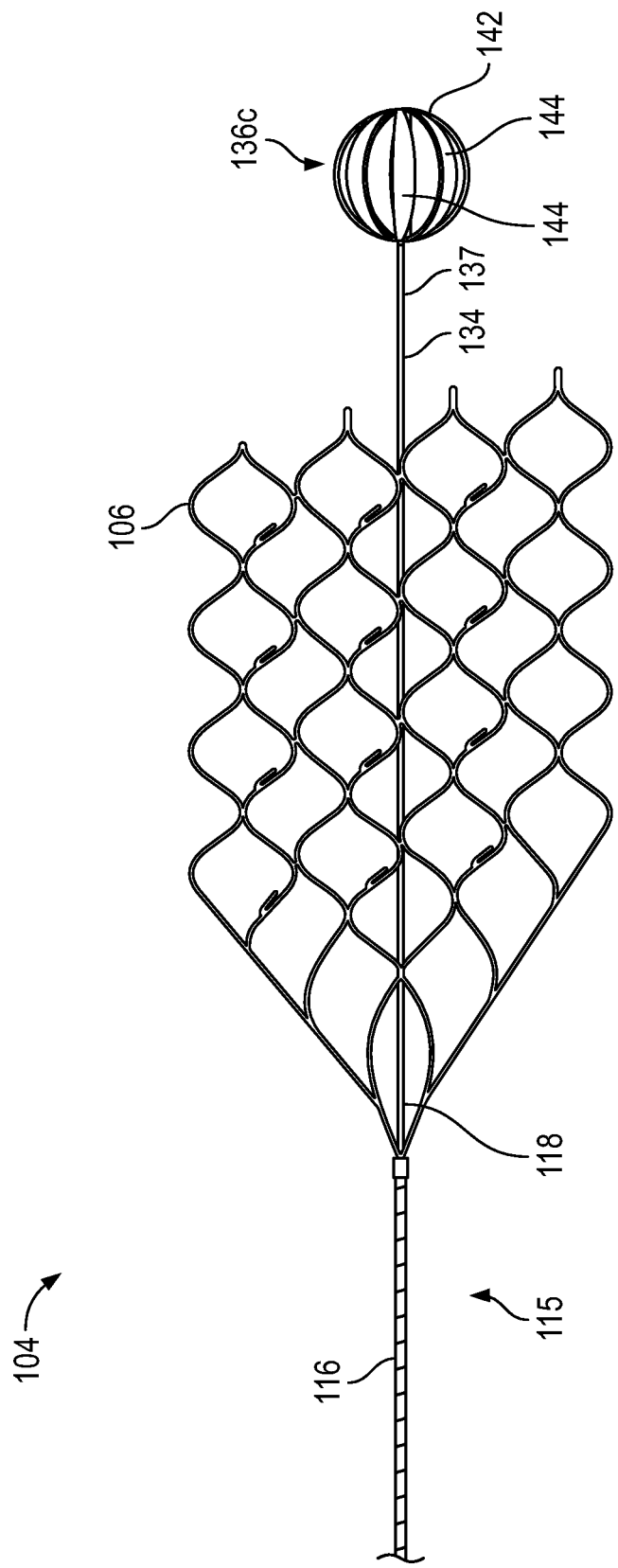

FIGS. 2-4 are side views of a portion of the treatment device 104 illustrating distal tips 136a-c with various geometries according to one or more embodiments of the present technology. FIG. 2 illustrates a distal tip 136a have a curved or hooked shape. As shown in FIG. 2, the distal tip 136a can form a "J" shape, with a first portion that extends distally from the main body 137 of the second conductor 118, a second portion that curves and/or extends laterally relative to the main body 137, and a third portion that extends proximally towards the main body 137. The length and curvature of the distal tip 136a can be varied as desired.

FIG. 3 illustrates a distal tip 136b having a helical or spiral shape. The distal tip 136b can extend distally from the main body 137 of the second conductor 118 and can have any suitable number of turns or coils (e.g., at least one, two, three, four, five, or more). Additionally, the coil size can of the distal tip 136b can varied as desired. For example, the distal tip 136b can have coils that increase in size (e.g., diameter) along a distal direction, decrease in size along a distal direction, are uniform in size, etc.

FIG. 4 illustrates a distal tip 136c having a spherical or spheroid shape. As illustrated in FIG. 4, the distal tip 136c includes a plurality of curved members 144 (e.g., wires, struts, strips) forming a partially hollowed sphere. The distal tip 136c can have a larger radial dimension and/or surface area compared to the main body 137 of the second conductor 118. In some embodiments, the distal tip 136c can be configured as an embolization protection element, for example, a basket, mesh, or filter, etc., configured to capture any fragments that separate from the thrombus during engagement with the interventional element 106.

Although FIGS. 2-4 illustrate certain examples of shapes for the distal tip of the second conductor 118, other shapes can also be used, such as a serpentine shape, a zig-zag shape, a circular or oval shape, a polygonal shape, or any suitable combination thereof. Additionally, the features of the distal tips 136a-c illustrated in FIGS. 2-4 can be combined with each other and/or any of the other embodiments described herein. Additionally, any of the geometries described herein in connection with the distal tip of the second conductor 118 can alternatively or additionally be incorporated into portions of the second conductor 118 that are proximal to the distal tip of the second conductor 118. For example, one or more portions of the main body 137 of the second conductor 118 can be formed with any of the "distal tip" geometries described herein (e.g., curved, helical, spherical, spheroidal, etc.).

Selected Embodiments of Waveforms for Electrically Enhanced Retrieval

In some embodiments, the present technology provides waveforms and related parameters that can be used with any of the embodiments described herein, such as the treatment system 100 and associated devices and methods described above with respect to FIGS. 1A-4, as well as other device configurations and techniques. In each of these embodiments, the waveforms and parameters can be beneficially employed to promote clot adhesion with little or no damage to surrounding tissue. Additionally, although the waveforms and parameters disclosed herein may be used for treating a cerebral or intracranial embolism, other applications and other embodiments in addition to those described herein are within the scope of the technology. For example, the waveforms and parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

While applying a continuous uniform DC signal to negatively charge the interventional element can improve its attachment to the thrombus, this approach may risk damage to surrounding tissue (e.g., ablation), and sustained current at a relatively high level may also be thrombogenic (i.e., may generate new clots). For achieving effective clot-grabbing without ablating tissue or generating substantial new clots at the target site, periodic waveforms (e.g., pulsed DC or AC waveforms) have been found to be particularly useful. Without wishing to be bound by theory, the clot-adhesion effect appears to be most closely related to the peak current of the delivered electrical signal. Periodic waveforms can advantageously provide the desired peak current without delivering excessive total energy or total electrical charge. In some embodiments, for example, periodic, non-square waveforms are well suited to deliver a desired peak current while reducing the amount of overall delivered energy or charge, e.g., as compared to either uniform applied DC waveforms or square waveforms.

In some embodiments, the periodic waveforms described herein are biphasic waveforms having a first phase with a first polarity (e.g., a positive polarity) and a second phase with a second, opposite polarity (e.g., a negative polarity). The first and second phases can be asymmetric so that the waveform results in application of a net charge to the interventional element. For example, the first phase can have a longer duration and/or a greater amplitude (e.g., peak current and/or voltage magnitude) than the second phase. In some embodiments, as discussed above, the waveform can have an intermittent negative polarity in that the waveform predominantly outputs a positive current interspersed with relatively short periods of negative current. This approach can advantageously reduce the risk of adverse events such as new clot formation or bubble formation at the treatment site.

Figure 5A:
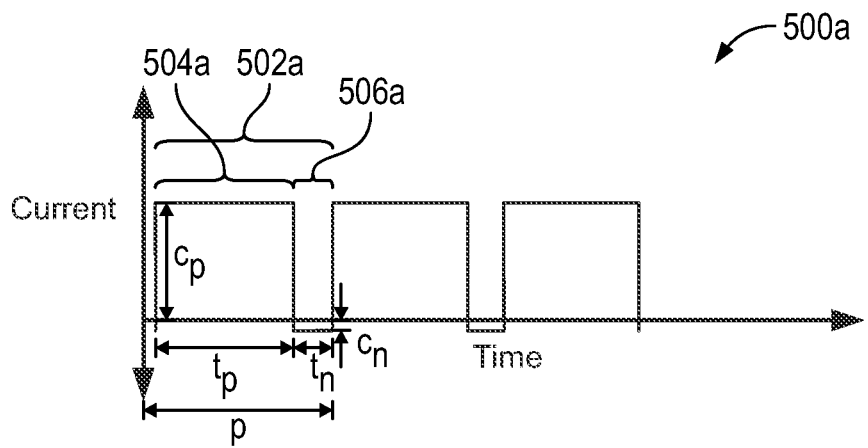
FIGS. 5A-5F illustrate representative examples of periodic waveforms, in accordance with one or more embodiments of the present technology.

FIG. 5A illustrates a square waveform 500a having intermittent negative polarity according to one or more embodiments of the present technology. The waveform 500a can be used with the devices and methods described above with respect to FIGS. 1A-4, as well as with other devices and techniques. The waveform 500a includes a repeating cycle 502a having a positive phase or signal portion 504a, and a negative phase or signal portion 506a. In the illustrated embodiment, the positive phase 504a is a positive square wave pulse and the negative phase 506a is a negative square wave pulse. In other embodiments, the positive phase 504a and/or the negative phase 506a can have a different shape, as described in greater detail below with respect to FIGS. 5B-5F.

As shown in FIG. 5A, the positive phase 504a has a duration or pulse width $t_p$, and the negative phase 506a has a duration or pulse width $t_n$. The duration $t_p$ of the positive phase 504a can be greater than the duration $t_n$ of the negative phase 506a, such that the waveform 500a predominantly delivers positive current. For example, the ratio of the duration $t_p$ to the period p of the waveform 500a (also referred to herein as the duty cycle of the positive phase 504a or the "positive duty cycle") can be at least 50%, 60%, 70%, 75%, 80%, 85%, 90%, 95%, or 99%. The ratio of the duration $t_n$ to the period p of the waveform 500a (also referred to herein as the duty cycle of the negative phase 506a or the "negative duty cycle") can be no more than 50%, 40%, 30%, 25%, 20%, 15%, 10%, 5%, or 1%.

In the illustrated embodiment, the positive phase 504a has a peak positive current $c_p$ and the negative phase 506a has a peak negative current $c_n$. The amplitude of the positive phase 504a (e.g., the magnitude of the peak positive current $c_p$) is greater than the amplitude of the negative phase 506a (e.g., the magnitude of the peak negative current $c_n$). The magnitude of the peak positive current $c_p$ can be at least 2 times, 5 times, 10 times, 15 times, 20 times, 25 times, 30 times, 35 times, 40 times, 45 times, or 50 times greater than the magnitude of the peak negative current $c_p$. In some embodiments, the peak positive current $c_p$ is within a range from 0.5 mA to 5 mA, or from 1 mA to 3 mA. The peak positive current $c_p$ can be less than or equal to 5 mA, 4 mA, 3 mA, 2.5 mA, 2 mA, 1.5 mA, 1 mA, or 0.5 mA. The peak negative current $c_n$ can be within a range from of –0.01 mA to –0.5 mA, or from –0.1 mA to –0.2 mA. In some embodiments, the peak negative current $c_n$ is greater than or equal to –0.5 mA, –0.4 mA, –0.3 mA, –0.2 mA, –0.175 mA, –0.15 mA, –0.125 mA, –0.1 mA, –0.075 mA, –0.05 mA, –0.025 mA, or –0.01 mA.

The waveform 500a can have any suitable frequency (e.g., corresponding to the inverse of the period p shown in FIG. 5A), such as a frequency within a range from 10 Hz to 100 kHz, or from 100 Hz to 10 kHz. In some embodiments, the waveform 500a has a frequency greater than or equal to 10 Hz, 100 Hz, 200 Hz, 300 Hz, 400 Hz, 500 Hz, 600 Hz, 700 Hz, 800 Hz, 900 Hz, 1 kHz, 2 kHz, 3 kHz, 4 kHz, 5 kHz, 6 kHz, 7 kHz, 8 kHz, 9 kHz, 10 kHz, 50 kHz, or 100 kHz.

FIGS. 5B-5F illustrate additional examples of periodic waveforms 500b-500e having intermittent negative polarity according to one or more embodiments of the present technology. The waveforms 500b-e can be used with the devices and methods described above with respect to FIGS. 1A-4, as well as with other devices and techniques. The characteristics of the waveforms 500b-500e can be generally similar to the waveform 500a of FIG. 5A (e.g., with respect to peak positive current $c_p$, peak negative current $c_n$, positive duty cycle, negative duty cycle, period, and/or frequency). Accordingly, like reference numbers and labels in FIGS. 5A-5F are used to identify similar or identical features, and the discussion of the waveforms 500b-500e of FIGS. 5B-5F will be limited to those features that differ from the waveform 500a of FIG. 5A.

Figure 5B:
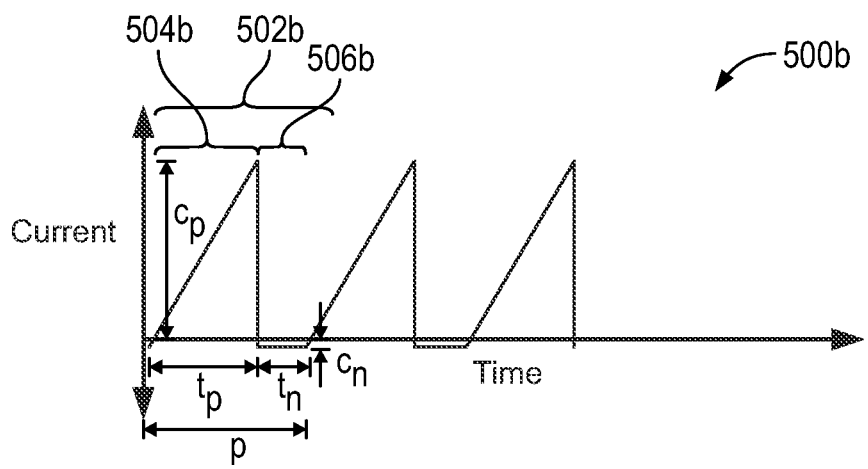

FIG. 5B illustrates a triangular waveform 500b. As shown in FIG. 5B, the triangular waveform 500b includes a repeating cycle 502b with a positive phase 504b and a negative phase 506b. The positive phase 504b has a triangular shape including an upward ramp followed by a sharp drop (e.g., a sawtooth shape), such that the peak positive current $c_p$ corresponds to the apex of the upward ramp. In other embodiments, however, the positive phase 504b can have a different shape, such as a sharp rise followed by a downward ramp (e.g., a reverse sawtooth shape), an upward ramp followed by a downward ramp (e.g., a symmetric triangular shape), etc. The negative phase 506b of the triangular waveform 500b can have a square shape, trapezoidal shape, triangular shape, or any other suitable shape. In some embodiments, the triangular waveform 500b has the same positive and negative amplitudes as the square waveform 500a of FIG. 5A, but the triangular waveform 500b is able to deliver the same peak current as the square waveform 500a, with only half of the total charge delivered and less total energy delivered.

Figure 5C:
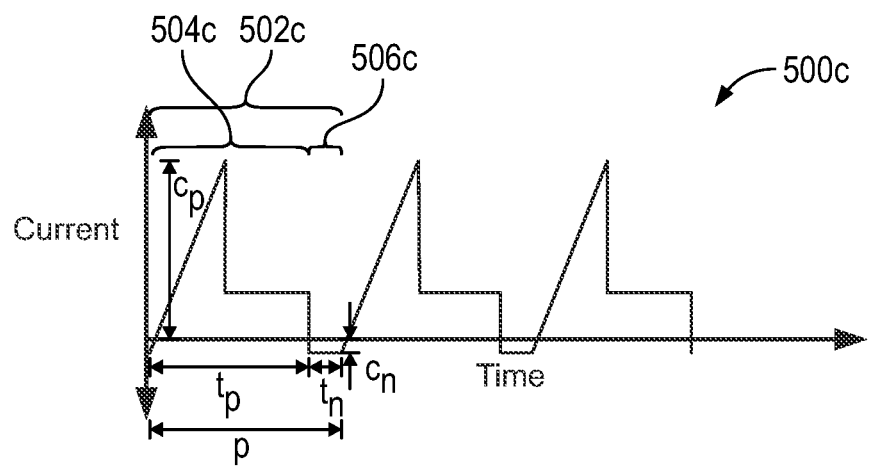

FIG. 5C illustrates a composite waveform 500c including a square waveform superimposed on a triangular waveform. The waveform 500c includes a repeating cycle 502c with a positive phase 504c and a negative phase 50bc. As shown in FIG. 5C, the positive phase 504c has a triangular (e.g., sawtooth) portion and a square portion. The triangular portion can have a greater peak positive current than the square portion, such that the peak positive current $c_p$ of the positive phase 504c corresponds to the peak current of the triangular portion. Alternatively, the square portion can have the same or a greater peak positive current than the triangular portion. Although FIG. 5C illustrates the triangular portion as preceding the square portion, in other embodiments, the square portion can precede the triangular portion. The negative phase 506c of the composite waveform 500c can have a square shape, trapezoidal shape, triangular shape, or any other suitable shape.

The composite waveform 500c shown in FIG. 5C can deliver additional efficacy compared to the triangular waveform 500b of FIG. 5B while delivering less overall energy than the square waveform 500a of FIG. 5A. This is because the delivered energy is proportional to the square of current and the brief high peak in the composite waveform 500c of FIG. 4C can ensure that current is supplied without dispensing excessive energy. In other embodiments, however, the composite waveform 500c can alternatively or additionally include other types of waveforms, such as trapezoidal waves, sinusoidal waves, etc. The composite waveform 500c can include any suitable number of superimposed waveforms, such as two, three, four, or more superimposed waveforms.

Figure 5D:
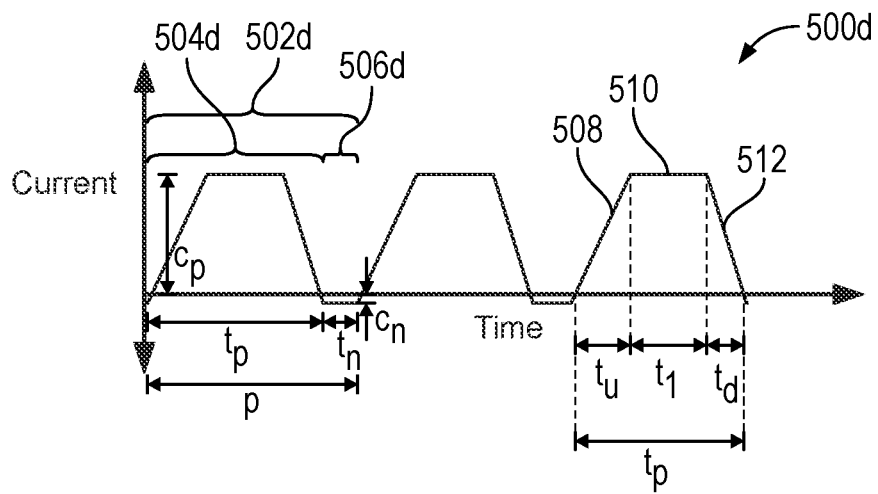

FIG. 5D illustrates a trapezoidal waveform 500d. The trapezoidal waveform 500d includes a repeating cycle 502d with a positive phase 504d and a negative phase 506d. In the illustrated embodiment, the positive phase 504d has a trapezoidal shape with an upward ramp 508 having a duration $t_u$, a flat portion 510 having a duration $t_1$, and a downward ramp 512 having a duration $t_d$. The peak positive current $c_p$ of the positive phase 504d can correspond to the current of the flat portion 510 of the positive phase 504d. In some embodiments, the upward and downward ramps 508, 512 at the beginning and end of each trapezoidal pulse can provide periods of reduced current compared to square waveforms. The respective durations $t_u$, $t_d$ of the upward and downward ramps 508, 512 can each independently be less than or equal to 20%, 15%, 10%, or 5% of the duration $t_p$ of the positive phase 504d, such as within a range from 5% to 10% of the duration $t_p$. The duration $t_u$ of the upward ramp 508 can be the same as the duration $t_d$ of the downward ramp 512, such that the trapezoidal pulses are symmetrical. Alternatively, the duration $t_u$ of the upward ramp 508 can be different (e.g., shorter or longer) than the duration $t_d$ of the downward ramp 512, such that the trapezoidal pulses are asymmetrical. The duration $t_1$ of the flat portion 510 can be greater than or equal to 80%, 85%, 90%, or 95% of the duration $t_p$, such as within a range from 90% to 95% of the duration $t_p$. The negative phase 506d of the trapezoidal waveform 500d can have a square shape, trapezoidal shape, triangular shape, or any other suitable shape.

Figure 5E:
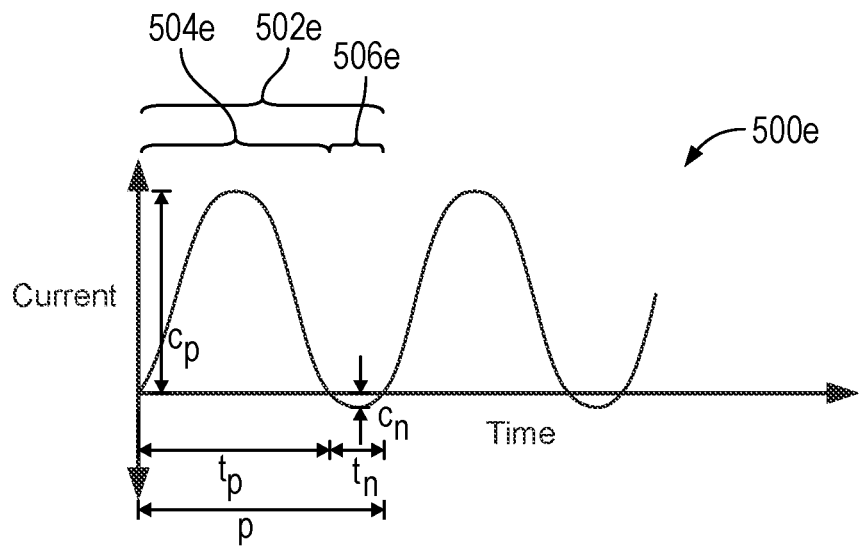

FIG. 5E illustrates a sinusoidal waveform 500e. The trapezoidal waveform 500e includes a repeating cycle 502e with a positive phase 504e and a negative phase 506e. As shown in FIG. 5E, the positive phase 504e has a positive sinusoidal pulse, with the apex of the pulse corresponding to the peak positive current $c_p$. The negative phase 506e has a negative sinusoidal pulse, with the apex of the pulse corresponding to the negative positive current $c_u$.

Figure 5F:
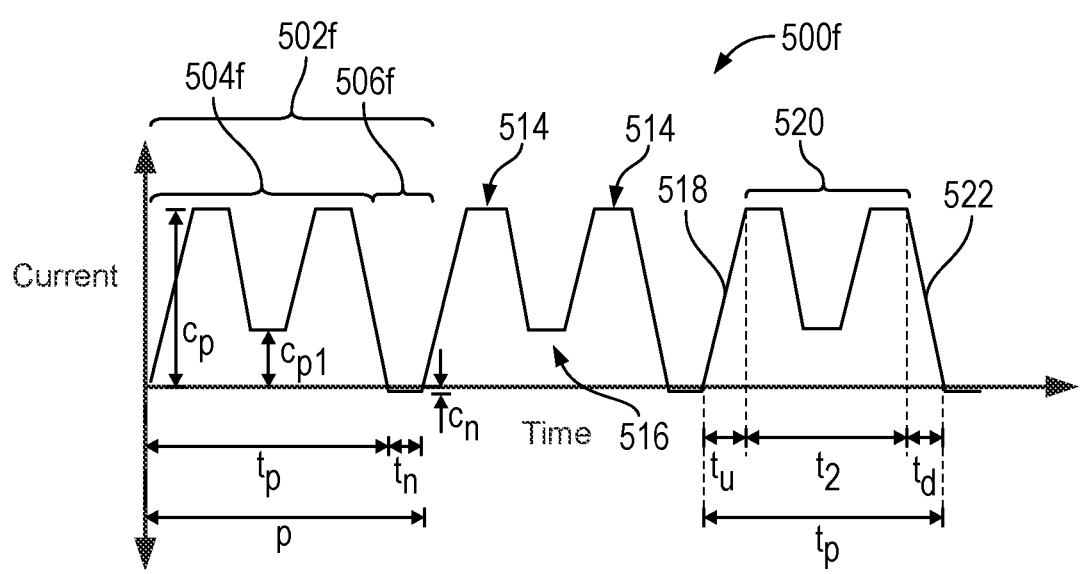

FIG. 5F illustrates a waveform 500f having a nested periodic pattern. The waveform 500f includes a repeating cycle 502f with a positive phase 504f and a negative phase 506f. The positive phase 504f includes a repeating pattern of pulses 514. Each pair of neighboring pulses 514 can be separated by an interpulse portion 516. The frequency of the repeating pattern of the positive phase 504f can be represented as n×f, where n is the number of repeated pulses 514 and f is the frequency of the overall waveform 500f. In the illustrated embodiment, the positive phase 504f includes a periodic trapezoidal waveform and the pulses 514 are trapezoidal pulses. In other embodiments, the positive phase 504f can include a different type of waveform (e.g., square, triangular, sinusoidal, etc., or a combination thereof) and/or a different number of pulses 514 (e.g., three, four, five, six, seven, eight, nine, ten, or more pulses 514). The negative phase 506f of the waveform 500f can have a square shape, trapezoidal shape, triangular shape, or any other suitable shape.

As shown in FIG. 5F, the peak current of each pulse 514 can correspond to the peak positive current $c_p$ of the positive phase 504f. The interpulse portion 516 can be a flat portion of the waveform having a constant or substantially constant current $c_{p1}$ that is less than the peak positive current $c_p$. For example, the current $c_{p1}$ of the interpulse portion 516 can be no more than 99%, 95%, 90%, 80%, 70%, 60%, 50%, 40%, 30%, 20%, or 10% of the peak positive current $c_p$, and/or within a range from 50% to 99% of the peak positive current $c_p$. The current $c_{p1}$ of the interpulse portion 516 can be greater than or equal to zero.

In the illustrated embodiment, the waveform of the positive phase 504f includes an upward ramp 518 having a duration $t_u$, an intermediate portion 520 having a duration $t_2$, and a downward ramp 522 having a duration $t_d$. The respective durations $t_u$, $t_d$ of the upward and downward ramps 518, 522 can each independently be less than or equal to 20%, 15%, 10%, or 5% of the duration $t_p$ of the positive phase 504f, such as within a range from 5% to 10% of the duration $t_p$. The duration $t_u$ of the upward ramp 518 can be the same as the duration $t_d$ of the downward ramp 522, or can be different (e.g., shorter or longer) than the duration $t_d$ of the downward ramp 522. The duration $t_2$ of the intermediate portion 520 can be greater than or equal to 80%, 85%, 90%, or 95% of the duration $t_p$, such as within a range from 90% to 95% of the duration $t_p$. Optionally, the upward ramp 518 can be omitted such that at the beginning of the positive phase 504f, the waveform 500f transitions instantaneously or near-instantaneously from zero current to the peak positive current $c_p$. Similarly, the downward ramp 522 can be omitted such that at the end of the positive phase 504f, the waveform 500f transitions instantaneously or near-instantaneously from the peak positive current $c_p$ to zero current.

Although FIGS. 5A-5F illustrate various examples of waveforms 500a-500e, in other embodiments, other types of waveforms can be used, depending on the desired power delivery characteristics and/or other considerations. For example, any non-square waveform, a superposition of a square waveform with any non-square waveform, etc., can be used with the devices and methods described above with respect to FIGS. 1A-4, as well as with other devices and techniques.

The characteristics of the waveforms described herein (e.g., the waveforms 500a-500e of FIGS. 5A-5F) can be configured to achieve desired power delivery parameters, such as overall electrical charge, total energy, and peak current delivered to the interventional element. For example, the overall electrical charge delivered to the interventional element can be within a range from 50 mC to 1500 mC, or from 100 mC to 1000 mC, or from 200 mC to 600 mC. In some embodiments, the total electrical charge delivered to the interventional element is less than or equal to 1500 mC, 1400 mC, 1300 mC, 1200 mC, 1100 mC, 1000 mC, 900 mC, 800 mC, 700 mC, 600 mC, 500 mC, 400 mC, 300 mC, 200 mC, or 100 mC. The total energy delivered to the interventional element can be within a range from 1 mJ to 5000 mJ, or from 50 mJ to 2000 mJ, or from 100 mJ to 1000 mJ. In some embodiments, the total energy delivered to the interventional element is less than or equal to 5000 mJ, 4000 mJ, 3000 mJ, 2000 mJ, 1500 mJ, 1000 mJ, 900 mJ, 800 mJ, 700 mJ, 600 mJ, 500 mJ, 400 mJ, 300 mJ, 200 mJ, 100 mJ, or 50 mJ.

The duration of signal delivery is another parameter that can be controlled to achieve the desired clot-adhesion effects without damaging tissue at the target site or generating new clots. In some embodiments, the total signal delivery time is no more than 15 minutes, 10 minutes, 9 minutes, 8 minutes, 7 minutes, 6 minutes, 5 minutes, 4 minutes, 3 minutes, 2 minutes, 1.5 minutes, 1 minutes, or 30 seconds. As used herein, the "total signal delivery time" refers to the time period during which the waveform is supplied to the interventional element (including those periods of time between pulses of current).

In some embodiments, the waveforms described herein are delivered during a single session having a total duration or signal delivery time of no more than 15 minutes, 10 minutes, 9 minutes, 8 minutes, 7 minutes, 6 minutes, 5 minutes, 4 minutes, 3 minutes, 2 minutes, 1.5 minutes, 1 minutes, or 30 seconds. Alternatively, the waveforms described herein can be delivered during multiple sessions, such as at least 2 sessions, 3 sessions, 4 sessions, 5 sessions, 6 sessions, 7 sessions, 8 sessions, 9 sessions, or 10 sessions. The individual sessions can each have the same duration, or some or all of the sessions can have different durations. In some embodiments, each session can independently have a duration of no more than 15 minutes, 10 minutes, 9 minutes, 8 minutes, 7 minutes, 6 minutes, 5 minutes, 4 minutes, 3 minutes, 2 minutes, 1.5 minutes, 1 minutes, or 30 seconds. For example, the waveforms described herein can be delivered over 3 sessions of 5 minutes each. The sessions can be spaced apart by at least 15 minutes, 10 minutes, 9 minutes, 8 minutes, 7 minutes, 6 minutes, 5 minutes, 4 minutes, 3 minutes, 2 minutes, 1.5 minutes, 1 minutes, or 30 seconds. The sessions can each use the same waveforms and/or power delivery parameters, or some or all of the sessions can use different waveforms and/or power delivery parameters.

FIGS. 6A and 6B are tables illustrating example waveform characteristics and power delivery parameters according to one or more embodiments of the present technology. The parameters in FIGS. 6A and 6B are calculated for a square waveform applied to a circuit having an assumed resistance of 1 kohm in the table of FIG. 6A, and an assumed resistance of 50 ohm in the table of FIG. 6B. The waveform characteristics and parameters in FIGS. 6A and 6B can be used with the devices and methods described above with respect to FIGS. 1A-4, as well as with other devices and techniques.

Conclusion

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. As used herein, the phrase "and/or" as in "A and/or B" refers to A alone, B alone, and A and B.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A system for removing a thrombus, the system comprising:
   an interventional element configured to engage and retrieve the thrombus within a blood vessel; and
   a signal generator in electrical communication with the interventional element, the signal generator configured to provide a voltage having a magnitude within a range from 2 volts to 28 volts, the signal generator further configured to deliver an electrical signal to the interventional element,
      wherein the electrical signal includes a waveform having:
         a positive phase having a peak positive current and a first duration, and
         a negative phase having a peak negative current and a second duration,
         wherein a magnitude of the peak positive current is greater than a magnitude of the peak negative current, and the first duration is greater than the second duration.

2. The system of claim 1, wherein the first duration is at least 70% of a period of the waveform.

3. The system of claim 1, wherein the second duration is no more than 30% of a period of the waveform.

4. The system of claim 1, wherein the magnitude of the peak positive current is at least 5 times greater than the magnitude of the peak negative current.

5. The system of claim 1 wherein the peak positive current is within a range from 1 mA to 5 mA.

6. The system of claim 1, wherein the peak negative current is within a range from −0.01 mA to −0.5 mA.

7. The system of claim 1, wherein the waveform has a frequency within a range from 100 Hz to 10 kHz.

8. The system of claim 1, wherein the waveform is a square waveform, a triangular waveform, a sawtooth waveform, a trapezoidal waveform, a sinusoidal waveform, or a combination thereof.

9. The system of claim 1, wherein the positive phase includes a plurality of repeated pulses.

10. The system of claim 9, wherein the plurality of repeated pulses includes a plurality of square pulses, triangular pulses, trapezoidal pulses, sinusoidal pulses, or a combination thereof.

11. The system of claim 9, wherein the positive phase includes two to ten repeated pulses.

12. The system of claim 1, wherein the interventional element includes a self-expanding mesh structure.

13. The system of claim 1, further comprising a core assembly including:
    a first conductor coupled to the interventional element, and
    a second conductor extending distally from the first conductor,
    wherein the signal generator is configured to deliver the electrical signal to the first and second conductors.

14. The system of claim 13, wherein the second conductor includes a distal tip having a linear, curved, hooked, helical, spiral, spherical, or spheroidal shape.

15. A method for removing a thrombus, comprising:
    applying a periodic electrical signal to an interventional element positioned near the thrombus in a blood vessel, the periodic electrical signal including:
       a positive signal portion having a peak positive current, and
       a negative signal portion having a peak negative current,
       wherein the peak positive current has a greater magnitude than the peak negative current, and wherein the positive signal portion has a greater duty cycle than the negative signal portion; and removing the thrombus with the interventional element.

16. The method of claim 15, wherein the positive signal portion has a duty cycle greater than or equal to 70%.

17. The method of claim 15, wherein the magnitude of the peak positive current is at least 5 times greater than the magnitude of the peak negative current.

18. The method of claim 15, wherein the interventional element forms a first electrode, and wherein the method further comprises applying the periodic electrical signal to at least one second electrode spaced apart from the first electrode.

19. The method of claim 18, wherein the at least one second electrode is located on a conductive element positioned in the blood vessel and spaced apart from the interventional element.

20. The method of claim 19, wherein the conductive element includes a main body and a distal tip connected to the main body, and wherein the distal tip forms the second electrode.

21. The system of claim 1, wherein the electrical signal is configured to cause electrostatic attraction of the thrombus to the interventional element.

22. The system of claim 1, wherein the electrical signal does not ablate surrounding tissue.

\* \* \* \* \*